United States Patent [19]

Sohn et al.

[11] Patent Number: 5,401,700
[45] Date of Patent: Mar. 28, 1995

[54] PLANT PROTECTION AGENTS BASED ON PYRAZOLECARBOXYLIC ACID DERIVATIVES

[75] Inventors: Erich Sohn, Augsburg; Hilmar Mildenberger, Kelkheim; Klaus Bauer, Hanau; Hermann Bieringer, Eppstein/Taunus, all of Germany

[73] Assignee: Hoechst Aktiengesellschaft, Frankfurt am Main, Germany

[21] Appl. No.: 912,659

[22] Filed: Jul. 13, 1992

Related U.S. Application Data

[63] Continuation of Ser. No. 324,300, Mar. 15, 1989, abandoned.

[30] Foreign Application Priority Data

Mar. 17, 1988 [DE] Germany ............... 38 08 896.7

[51] Int. Cl.$^6$ .......................................... A01N 25/32
[52] U.S. Cl. ................................ 504/106; 504/138; 504/139; 504/105
[58] Field of Search ................ 71/92, 88; 504/105, 504/106, 138, 139, 270, 281

[56] References Cited

U.S. PATENT DOCUMENTS

| | | | |
|---|---|---|---|
| 4,130,413 | 12/1978 | Handte et al. | 71/92 |
| 4,420,324 | 12/1983 | Eicken et al. | 71/92 |
| 4,620,865 | 11/1986 | Beck et al. | 71/92 |
| 4,681,618 | 7/1987 | Gehring et al. | 71/92 |
| 4,752,326 | 6/1988 | Ohyama et al. | 71/92 |
| 4,775,406 | 10/1988 | Schmierer et al. | 71/86 |
| 4,787,930 | 11/1988 | Gehring et al. | 71/92 |
| 4,891,057 | 1/1990 | Sohn et al. | 71/92 |

FOREIGN PATENT DOCUMENTS

| | | |
|---|---|---|
| 508225 | 7/1978 | Australia . |
| 50884/85 | 6/1986 | Australia . |
| 1242092 | 9/1988 | Canada . |
| 0151866A2 | 8/1985 | European Pat. Off. . |
| 0152006 | 8/1985 | European Pat. Off. . |
| 3442690 | 5/1986 | Germany . |
| 3444918 | 6/1986 | Germany . |
| 153762 | 6/1967 | Hungary . |

OTHER PUBLICATIONS

Chem. Abstract Bd., vol. 68 (1968) 87293.

Primary Examiner—Allen J. Robinson
Assistant Examiner—John D. Pak
Attorney, Agent, or Firm—Curtis Morris & Safford

[57] ABSTRACT

The present invention relates to agents for protecting crop plants from the phytotoxic side effects of herbicides, which agents contain a compound of the formula

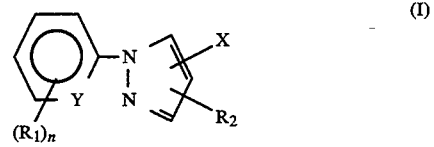

(I)

wherein
Y denotes C—H or N,
the symbols $R_1$ independently of one another denote alkyl, halo-alkyl, alkoxy, haloalkoxy or halogen,
$R_2$ denotes alkyl or cycloalkyl,
X denotes $COOR_3$, $CON(R_4)_2$, $COSR_3$, CN or

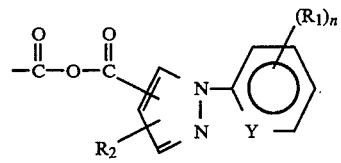

$R_3$ denotes an alkali metal or alkaline earth metal, hydrogen, alkyl, alkenyl, alkynyl, cycloalkyl, or phenylalkyl, it being possible for phenyl to be substituted by halogen, or trisalkylsilylalkyl or alkoxyalkyl,
the symbols $R_4$ independently of one another denote H, alkyl or cycloalkyl, which can be substituted, or radicals $R_4$ together with the N atom linking them form a 4- to 7-membered heterocyclic ring and
n denotes 1 to 3,
in combination with a herbicide.

4 Claims, No Drawings

PLANT PROTECTION AGENTS BASED ON PYRAZOLECARBOXYLIC ACID DERIVATIVES

This application is a continuation of application Ser. No. 07/324,300, filed Mar. 15, 1989, now abandoned.

DESCRIPTION

The present invention relates to agents for protecting crop plants from the phytotoxic side effects of herbicides, which agents contain a compound of the formula I

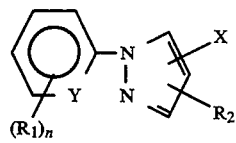

wherein
Y denotes C—H or N,
the symbols $R_1$ independently of one another denote ($C_1$–$C_4$)-alkyl, ($C_1$–$C_4$)-haloalkyl, ($C_1$–$C_4$)alkoxy, ($C_1$–$C_4$)-haloalkoxy or halogen,
R2 denotes ($C_1$–$C_{12}$)-alkyl or ($C_3$–$C_7$)-cycloalkyl,
X denotes $COOR_3$, $CON(R_4)_2$, $COSR_3$, CN or

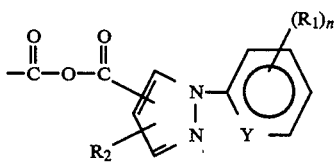

$R_3$ denotes an alkali metal or alkaline earth metal, hydrogen, ($C_1$–$C_{10}$)-alkyl, ($C_3$–$C_{20}$)-alkenyl, ($C_3$–$C_{10}$)-alkynyl, ($C_3$–$C_7$)-cycloalkyl or phenyl-($C_1$–$C_4$)-alkyl, it being possible for phenyl to be substituted by halogen, or tris-($C_1$–$C_4$)-alkyl-silyl ($C_1$–$C_4$)-alkyl or ($C_1$–$C_4$)-alkoxy-($C_1$–$C_4$)-alkyl,
the symbols $R_4$ independently of one another denote H, ($C_1$–$C_{10}$)-alkyl or ($C_3$–$C_7$)-cycloalkyl, which can be substituted, or 2 radicals $R_4$ together with the N atom linking them form a 4- to 7-membered heterocyclic ring and
n denotes 1 to 3,
in combination with a herbicide.

In this formula, alkyl denotes straight-chain or branched alkyl.

In the case where

X = 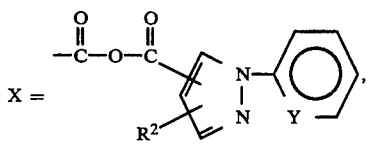

two identical radicals of a compound of the formula I are linked to one another.

Halogen preferably denotes chlorine or bromine, alkali metal preferably denotes Li, Na or K and alkaline earth metal denotes in particular Ca. The heterocyclic ring formed from the two radicals $R_4$ together with the N atom is preferably pyrrolidine, morpholine, 1,2,4-triazole or piperidine.

The compounds of the formula I in which Y denotes CH, $R_1$ denotes halogen or ($C_1$–$C_4$)-haloalkyl, $R_2$ denotes ($C_1$–$C_6$)-alkyl, X denotes $COOR_3$, $R_3$ denotes H or ($C_1$–$C_6$)-alkyl and n denotes 1 or 2 are furthermore preferred.

The compounds of the formula I in which Y denotes CH, $R_1$ denotes Cl, Br or $CF_3$, $R_2$ denotes ($C_1$–$C_4$)-alkyl, X denotes $COOR_3$, $R_3$ denotes ($C_1$–$C_4$)-alkyl and n denotes 2 are particularly preferred.

The compounds of the formula I in which Y denotes CH, $R_1$ denotes 2,4-$Cl_2$, $R_2$ denotes isopropyl, X denotes $COOR_3$ and $R_3$ denotes ($C_1$–$C_{10}$)-alkyl are novel and the present invention likewise relates to them. In these compounds, the 5-position is preferred for $R_2$ and the 3-position is preferred for X. The compound in which Y denotes CH, $R_1$ denotes 2,4-$Cl_2$, $R_2$ denotes 5-isopropyl and X denotes 3-$COOC_2H_5$ is of particular importance.

The compounds of-the formula I can be prepared by methods which are known from the literature (HU-PS 153,762 or Chem. Abstr. 68, 87293 y (1968)). For further derivatization, the radical —$COOR_3$ is converted into other radicals mentioned for X in a known manner, for example by hydrolysis, transesterification, amidation, salt formation and the like, as is described, for example, in DE-OS 3,444,918 or 3,442,690.

When plant treatment agents, in particular herbicides, are used, undesirable damage which cannot be tolerated may occur to crop plants. On application of herbicides after emergence of the crop plants, in particular, there is therefore often the need to avoid the risk of possible phytotoxicity.

Various compounds have already been described for this use (for example EP-A 152,006).

Surprisingly, it has been found that compounds of the formula I have the property of preventing or completely eliminating phytotoxic side effects of plant protection agents, in particular herbicides, when used in crops of useful plants. The compounds of the formula I are capable of completely eliminating the harmful side effects of herbicides without curtailing the activity of these herbicides against harmful plants.

Such compounds which have the property of protecting crop plants from phytotoxic damage by herbicides without impairing the actual herbicidal action of these agents are called "antidotes" or "safeners".

The field of use of conventional herbicides can be widened quite considerably by addition of the safener compound of the formula I.

The present invention thus also relates to a method of protecting crop plants from the phytotoxic side effects of plant protection agents, in particular herbicides, which comprises treating the plants, plant seeds or cultivation areas with a compound of the formula I before, after or at the same time as the plant protection agent.

Herbicides of which the phytotoxic side effects can be reduced by means of the compounds of the formula I are, for example, carbamates, thiocarbamates, halogenoacetanilides, substituted phenoxy-, naphthoxy- and phenoxy-phenoxy-carboxylic acid derivatives and heteroaryloxyphenoxycarboxylic acid derivatives, such as quinolyloxy-, quinoxalyloxy-, pyridyloxy-, benzoxazolyloxy- and benzothiazolyloxy-phenoxy-carboxylic acid esters, and furthermore dimedoneoxime derivatives. Of these, phenoxy-phenoxy- and heteroaryloxyphenoxy-carboxylic acid esters are preferred. Possible esters here are, in particular, lower alkyl, alkenyl and alkynyl esters.

The following herbicides may be mentioned as examples, without a limitation being intended by these:

A) Herbicides of the ($C_1$–$C_4$)-alkyl, ($C_2$–$C_4$)-alkenyl or ($C_3$–$C_4$)-alkynyl phenoxyphenoxy- and heteroaryloxyphenoxycarboxylate type, such as methyl 2-(4-(2,4-dichlorophenoxy)-phenoxy)-propionate,
methyl 2-(4-(4-bromo-2-chlorophenoxy)-phenoxy)-propionate,
methyl 2-(4-(4-trifluoromethylphenoxy)-phenoxy)-propionate,
methyl 2-(4-(2-chloro-4-trifluoromethylphenoxy)-phenoxy)-propionate,
methyl 2-(4-(2,4-dichlorobenzyl)-phenoxy)-propionate, 2-isopropylideneamino-oxyethyl (R)-2-[4-(6-chloro-quinoxalin-2-yloxy)-phenoxy]-propionate (propaquizafop),
ethyl 4-(4-(4-trifluoromethylphenoxy)-phenoxy)-pent-2-enoate,
ethyl 2-(4-(3,5-dichloropyridyl-2-oxy)-phenoxy)propionate,
propargyl 2-(4-(3,5-dichloropyridyl-2-oxy)-phenoxy)-propionate,
ethyl 2-(4-(6-chlorobenzoxazol-2-yl-oxy)-phenoxy)-propionate,
ethyl 2-(4-(6-chlorobenzothiazol-2-yl-oxy)-phenoxy)-propionate,
methyl 2-(4-(3-chloro-5-trifluoromethyl-2-pyridyloxy)-phenoxy)-propionate,
butyl 2-(4-(5-trifluoromethyl-2-pyridyloxy)-phenoxy)propionate,
ethyl 2-(4-(6-chloro-2-quinoxalyloxy)-phenoxy)propionate,
ethyl 2-(4-(6-fluoro-2-quinoxalyloxy)-phenoxy)propionate,
propargyl 2-(4-(5-chloro-3-fluoro-pyridyl-2-oxy)-phenoxy)-propionate,
ethyl 2-(4-(6-chloro-2-quinolyloxy)-phenoxy)-propionate,
trimethylsilylmethyl 2-(4-(3,5-dichloropyridyl-2-oxy)-phenoxy)-propionate,
ethyl 2-(4-(3-chloro-5-trifluoromethoxy-2-pyridyloxy)-phenoxy)-propionate, B) Chloroacetanilide herbicides, such as
N-methoxymethyl-2,6-diethyl-chloroacetanilide,
N-(3'-methoxyprop-2'-yl)-methyl-6-ethyl-chloroacetanilide and
N-(3-methyl-1,2,4-oxdiazol-5-yl-methyl)-chloroacetic acid 2,6-dimethylanilide, C) Thiocarbamates, such as
S-ethyl N,N-dipropylthiocarbamate or
S-ethyl N,N-diisobutylthiocarbamate D) Dimedone derivatives, such as
2-(N-ethoxybutyrimidoy L)-5-(2-ethylthiopropyl)-3-hydroxy-2-cyclohexen-1-one,
2-(N-ethoxybutyrimidoy l)-5-(2-phenylthiopropyl)-3-hydroxy-2-cyclohexen-1-one,
2-(1-allyloxyiminobuty l)-4-methoxycarbonyl-5,5-dimethyl-3-oxocyclohexenol,
2-(N-ethoxypropionamidoyl)-5-mesityl-3-hydroxy-2-cyclohexen-1-one,
2-(N-ethoxybutyrimidoyl)-3-hydroxy-5-(thian-3-yl)-2-cyclohexen-1-one,
2-[1-(ethoxyimino)-butyl]-3-hydroxy-5-(2H-tetrahydrothiopyran-3-yl)-2-cyclohexen-1-one (BASF 517),
2-[1-(ethoxyimino)-propyl]-3-hydroxy-5-mesitylcyclohex-2-enone (PP 604 from ICI) and
(+)-2-[(E)-3-chloroallyloxyiminopropyl]-5-(2-ethylthiopropyl)-3-hydroxycyclohex-2-enone (clethodim).

Of the herbicides which can be combined according to the invention with the compounds of the formula I, the compounds listed under A) may be mentioned as preferred, in particular ethyl 2-(4-(6-chlorobenzoxazol-2-yl-oxy)-phenoxy)-propionate, ethyl 2-(4-(6-chlorobenzothiazol-2-yl-oxy)-phenoxy)-propionate and propargyl 2-(4-(5-chloro-3-fluoropyridyl-2-oxy)-phenoxy)-propionate. Of the substances mentioned under D), 2-(N-ethoxypropionamidoyl)5-mesityl-3-hydroxy-2-cyclohexen-1-one is of particular importance.

The ratio of the amounts of safener (compound I): herbicide can vary within wide limits of between 1:10 and 10:1, in particular between 2:1 and 1:10.

The particular optimum amounts of herbicide and safener depend on the type of herbicide used or on the type of safener used and on the nature of the plant crop to be treated, and can be determined from case to case by appropriate experiments.

The main fields of use for application of the safeners are, above all, cereal crops (wheat, rye, barley and oats), rice, maize and sorghum, and also cotton, sugarbeet, cane sugar and soya bean.

Depending on their properties, the safeners can be used for pretreatment of the seeds of the crop plants (dressing of the seeds) or can be introduced into the seed furrows before sowing or used together with the herbicide before or after emergence of the plants. Preemergence treatment includes both treatment of the cultivation area before sowing and treatment of the sown cultivation areas on which there is as yet no growth.

However, simultaneous use of the antidote with the herbicide in the form of tank mixes or finished formulations is preferred.

The compounds of the formula I or the combination thereof with one or more of the herbicides or herbicide groups mentioned can be formulated in various ways as determined by the biological and/or chemical-physical parameters. Suitable formulation possibilities are therefore: wettable powders (WP), emulsifiable concentrates (EC), aqueous solutions (SC), emulsions, sprayable solutions, oil- or water-based dispersions (SC), suspoemulsions (SC), dusting agents (DP), dressing agents, granules in the form of micro, spray, coated and adsorption granules, water-dispersible granules (WG), ULV formulations, microcapsules or waxes.

These individual types of formulation are known in principle and are described, for example, in: Winnacker-Küchler, "Chemische Technologie (Chemical Technology)", Volume 7, C. Hauser Verlag München, 4th edition 1986; van Falkenberg, "Pesticides Formulations", Marcel Dekker N.Y., 2nd edition, 1972-73; and K. Martens, "Spray Drying Handbook", 3rd edition 1979, G. Goodwin Ltd. London.

The formulation auxiliaries needed, such as inert materials, surfactants, solvents and other additives, are likewise known and are described, for example, in: Watkins, "Handbook of Insecticide Dust Diluents and Carriers" 2 nd edition, Darland Books, Caldwell N.J,; H. v. Olphen, "Introduction to Clay Colloid Chemistry", 2nd edition, Wiley & Sons, N.Y.; Marschen, "Solvents Guide", 2nd edition, Interscience, N.Y. 1950; McCutcheon's, "Detergents and Emulsifiers Annual", MC Publ. Corp., Ridgewood N.J.; Sisley and Wood, "Encyclopedia of Surface Active Agents, Chem. Publ. Co. Inc., N.Y. 1964; Schönfeldt, "Grenzflächenaktive Äthylenoxidaddukte (Surface-active ethylene oxide adducts)", Wiss. Verlagsgesell., Stuttgart 1976; and Winnacker-Küchler, "Chemische Technologie (Chemical Technology)", Volume 7, C. Hauser Verlag München, 4th edition 1986.

On the basis of these formulations, it is also possible to prepare combinations with other pesticidally active substances, fertilizers and/or growth regulators, for example in the form of a finished formulation or as a tank mix. Wettable powders are preparations which are uniformly dispersible in water and, in addition to the active compound and apart from a diluent or inert substance, also contain wetting agents, for example polyoxyethylated alkylphenols, polyoxyethylated fatty alcohols and alkyl- or alkylphenol-sulfonates, and dispersing agents, for example sodium lignin-sulfonate, sodium 2,2'-dinaphthylmethane-6,6'-disulfonate, sodium dibutyl-naphthalene-sulfonate or sodium oleyl-methyl-taurate. Emulsifiable concentrates are prepared by dissolving the active compound in an organic solvent, for example butanol, cyclohexanone, dimethylformamide, xylene or higher-boiling aromatics or hydrocarbons, with the addition of one or more emulsifiers. Examples of emulsifiers which can be used are: calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters. Dusts are obtained by grinding the active compound with finely divided solid substances, for example talc or naturally occurring clays, such as kaolin, bentonite, pyrophyllite or diatomaceous earth. Granules can be prepared either by spraying the active compound onto an adsorbent granular inert material or by applying active compound concentrates to the surface of carrier substances, such as sand, kaolinires or a granular inert material, by means of adhesives, for example polyvinyl alcohol, sodium polyacrylate or mineral oils. Suitable active compounds can also be granulated in the manner customary for the preparation of fertilizer granules if desired as a mixture with fertilizers.

The active compound concentration in wettable powders is, for example, about 10 to 90% by weight, the remainder to make up to 100% by weight consisting of customary formulation constituents. The active compound concentration in emulsifiable concentrates can be about 5 to 80% by weight. Dust-like formulations usually contain 5 to 20% by weight of active compound, and sprayable solutions contain about 2 to 20% by weight. In granules, the active compound content partly depends on whether the active compound is in the liquid or solid form and on what granulation auxiliaries, fillers and the like are used.

The active compound formulations mentioned additionally contain, if appropriate, the particular customary tackifiers, wetting agents, dispersing agents, emulsifiers, penetration agents, solvents, fillers or carrier substances.

For use, the concentrates in the commercially available form are diluted in the customary manner if appropriate, for example by means of water in the case of wettable powders, emulsifiable concentrates, dispersions and in some cases also microgranules. Dust-like and granular formulations and sprayable solutions are usually not further diluted with more inert substances before use.

The application amount required for the compounds of the formula I varies according o the external conditions, such as temperature, humidity, nature of the herbicide used and others. It can vary within wide limits, for example between 0.005 and 10.0 kg/ha or more of active substance, but is preferably between 0.01 and 5 kg/ha.

The following examples serve to illustrate the invention:

A. Formulation Examples a) A dusting agent is obtained by mixing 10 parts by weight of a compound of the formula I and 90 parts by weight of talc or an inert substance and comminuting the mixture in an impact mill.

b) A wettable powder which is readily dispersible in water is obtained by mixing 25 parts by weight of a compound of the formula I, 64 parts by weight of kaolin-containing quartz, as an inert substance, 10 parts by weight of potassium lignin-sulfonate and 1 part by weight of sodium oleoyl-methyl-taurate, as the wetting and dispersing agents, and grinding the mixture in a pinned disk mill.

c) A dispersion concentrate which is readily dispersible in water is obtained by mixing 20 parts by weight of a compound of the formula I with 6 parts by weight of alkylphenol polyglycol ether ((R)Triton X 207), 3 parts by weight of isotridecanol polyglycol ether (8 mol of ethylene oxide) and 71 parts by weight of paraffinic mineral oil (boiling range, for example, about 255 to more than 277° C.) and grinding the mixture to a fineness of less than 5 microns in a bead mill.

d) An emulsifiable concentrate is obtained from 15 parts by weight of a compound of the formula I, 75 parts by weight of cyclohexanone, as the solvent, and 10 parts by weight of oxyethylated nonylphenol, as the emulsifier.

e) A concentrate which is readily emulsifiable in water and consists of a phenoxycarboxylic acid ester and an antidote (10:1) is obtained from:

2.00% by weight of ethyl 2-(4-(6-chlorobenzoxazol-2yl-oxy)-phenoxy)-propionate
1.20% by weight of a compound of the formula I
69.00% by weight of xylene
7.80% by weight of calcium dodecylbenzenesulfonate
6.00% by weight of ethoxylated nonylphenol (10 mol of ethylene oxide) and
4.00% by weight of ethoxylated castor oil (40 mol of ethylene oxide)

The formulation is carried out as described under Example a), f) A concentrate which is readily emulsifiable in water and consists of a phenoxycarboxylic acid ester and an antidote (1:10) is obtained from:

4.0% by weight of ethyl 2-(4-(6-chlorobenzoxazol-2yl-oxy)-phenoxy)-propionate
40.0% by weight of a compound of the formula I
30.0% by weight of xylene
20.0% by weight of cyclohexanone
4.0% by weight of calcium dodecylbenzenesulfonate and
2.0% by weight of ethoxylated castor oil (40 mol of ethylene oxide)

B. Chemical Examples

1. Ethyl 1-(4-chlorophenyl)-5(3)-methyl-pyrazole-3(5)-carboxylate 4.3 g of 4-chlorophenylhydrazine II and 0.1 g of p-toluenesulfonic acid are added to 15.8 g of ethyl acetylpyruvate I in 100 ml of toluene with stirring and the mixtures heated, using a water separator. When no further water passes over, the mixture is allowed to cool and is diluted with 100 ml of toluene and washed with 100 ml of 3 N hydrochloric acid, 00 ml of water, 100 ml of saturated $NaHCO_3$ solution and 100 ml of water, and the organic phase is concentrated to dryness and chromatographed over silica gel (mobile phase petroleum ether > ethyl acetate).

Example No.

1 Ethyl 1-(4-chlorophenyl)-5-methyl-pyrazole-3-carboxylate (melting point 121°–124° C.)

62 Ethyl 1-(4-chlorophenyl)-3-methyl-pyrazole-5-carboxylate (oil)

Pyrazoles with a different substitution pattern in the aromatic part and/or a different allyl radical are prepared analogously and if appropriate derivatized on the carbonyl function. The derivatives are summarized in Table I.

TABLE I

Alkyl-aryl-pyrazolecarboxylic acid derivatives (I)

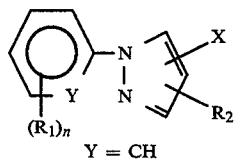

Y = CH

| Example No. | $(R_1)_n$ | $R_2$ | X | Melting point/boiling point mm Hg [°C.] |
|---|---|---|---|---|
| 2 | 4-Cl | 5-$CH_3$ | 3-$COOCH_3$ | |
| 3 | " | " | 3-COO-n-$C_3H_7$ | |
| 4 | " | " | 3-COO-i-$C_3H_7$ | |
| 5 | " | " | 3-COO-n-$C_4H_9$ | |
| 6 | " | " | 3-COO-n-$C_5H_{11}$ | |
| 7 | " | " | 3-COO-n-$C_6H_{13}$ | |
| 8 | " | " | 3-COO-n-$C_8H_{17}$ | |
| 9 | " | " | 3-COO-n-$C_{10}H_{21}$ | |
| 10 | " | " | (see structure below) | |

$$3\text{-}\underset{\underset{R_2}{\phantom{|}}}{C}(=O)\text{-}O\text{-}C(=O)\text{-pyrazole-N-N-aryl-}(R_1)_n$$

| | | | | |
|---|---|---|---|---|
| 11 | " | " | 3-COOH | 157–160 |
| 12 | " | " | 3-COOLi | |
| 13 | " | " | 3-COONa | |
| 14 | " | " | 3-COOK | |
| 15 | " | " | 3-$COOCa_{1/2}$ | |
| 16 | " | " | 3-COO-c-$C_4H_7$ | |
| 17 | " | " | 3-COO-c-$C_6H_{13}$ | |
| 18 | " | " | 3-$COOCH_2$—$C_6H_5$ | |
| 19 | " | " | 3-$COCCH_2$-(2,4-$Cl_2$—$C_6H_3$) | |
| 20 | " | " | 3-$COOCH_2CHCH_2$ | |
| 21 | " | " | 3-$COOC_2H_4CHCH_2$ | |
| 22 | " | " | 3-COO-n-$C_8H_{16}CHCH_2$ | |
| 23 | " | " | 3-$COOCH_2CCH$ | |
| 24 | " | " | 3-COO—$C_2H_4$—CCH | |
| 25 | " | " | 3-COO-n-$C_5H_{10}CCH$ | |
| 26 | " | " | 3-$COOCH_2Si(CH_3)_3$ | |
| 27 | " | " | 3-$COOC_2H_4OCH_3$ | |
| 28 | " | " | 3-$CONH_2$ | |
| 29 | " | " | 3-CN | |
| 30 | " | " | 3-$CONHCH_3$ | |
| 31 | 4-Cl | 5-$CH_5$ | 3-$CONHC_2H_5$ | |
| 32 | " | " | 3-CONH-n-$C_3H_7$ | |
| 33 | " | " | 3-CONH-n-$C_4H_9$ | |
| 34 | " | " | 3-CONH-n-$C_6H_{13}$ | |
| 35 | " | " | 3-CONH-n-$C_{10}H_{21}$ | |
| 36 | " | " | 3-CONH-i-$C_3H_7$ | |
| 37 | " | " | 3-$CON(CH_3)_2$ | |
| 38 | " | " | 3-$CON(CH_3)(nC_6H_{13})$ | |
| 39 | " | " | 3-$CON(C_2H_5)_2$ | |
| 40 | " | " | 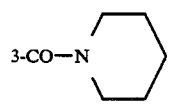 | |

TABLE I-continued

Alkyl-aryl-pyrazolecarboxylic acid derivatives

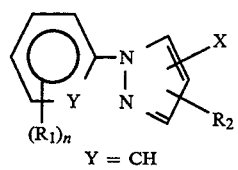

Y = CH (I)

| Example No. | $(R_1)_n$ | $R_2$ | X | Melting point/ boiling point mm Hg [°C.] |
|---|---|---|---|---|
| 41 | " | " | 3-CO—N(pyrrolidinyl) | |
| 42 | " | " | 3-CO—N(morpholinyl) | |
| 43 | " | " | 3-CO—N(2,6-dimethylmorpholinyl) | |
| 44 | " | " | 3-CO—NH-c-$C_6H_{11}$ | |
| 45 | " | " | 3-CO—NH-c-$C_3H_5$ | |
| 46 | " | " | 3-CO—N($CH_3$)(c$C_6H_{11}$) | |
| 47 | " | " | 3-COSH | |
| 48 | " | " | 3-COSNa | |
| 49 | " | " | 3-COS$CH_3$ | |
| 50 | " | " | 3-COS$C_2H_5$ | |
| 51 | " | " | 3-COS$CH_2C_6H_5$ | |
| 52 | " | " | 3-COS-n$C_8H_{17}$ | |
| 53 | " | " | 3-COS$C_2H_4OCH_3$ | |
| 54 | " | " | 3-COS$CH_2CHCH_2$ | |
| 55 | " | " | 3-COS$CH_2CCH$ | |
| 56 | " | " | 3-COS-c-$C_6H_{11}$ | |
| 57 | " | " | 3-COS$CH_2Si(CH_3)_3$ | |
| 58 | " | " | 3-COS-n-$C_4H_8CH(CH_3)_2$ | |
| 59 | " | " | 3-CON(imidazolyl) | |
| 60 | " | " | 3-COO$C_2H_4CH(CH_3)_2$ | |
| 61 | 4-Cl | 3-$CH_3$ | 5-COO$CH_3$ | |
| 63 | " | " | 5-COOn$C_3H_7$ | |
| 64 | " | " | 5-COO-i-$C_3H_7$ | |
| 65 | " | " | 5-COO-n-$C_4H_9$ | |
| 66 | " | " | 5-COO-n-$C_5H_{11}$ | |
| 67 | " | " | 5-COO-n-$C_6H_{13}$ | |
| 68 | " | " | 5-COO-n-$C_8H_{17}$ | |
| 69 | " | " | 5-COO-n-$C_{10}H_{21}$ | |
| 70 | " | " | 5-C(O)-O-C(O)-pyrazole-aryl (dimer) | |
| 71 | " | " | 5-COOH | |
| 72 | " | " | 5-COOLi | |
| 73 | " | " | 5-COONa | |
| 74 | " | " | 5-COOK | |
| 75 | " | " | 5-COO$Ca_{1/2}$ | |
| 76 | " | " | 5-COO-c-$C_4H_7$ | |
| 77 | " | " | 5-COO-c-$C_6H_{11}$ | |
| 78 | " | " | 5-COO$CH_2$—$C_6H_5$ | |
| 79 | " | " | 5-COO$CH_2$-(2,4-$Cl_2$—$C_6H_3$) | |

TABLE I-continued
Alkyl-aryl-pyrazolecarboxylic acid derivatives

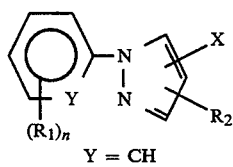

$Y = CH$ (I)

| Example No. | $(R_1)_n$ | $R_2$ | X | Melting point/ boiling point mm Hg [°C.] |
|---|---|---|---|---|
| 80 | " | " | 5-COOCH$_2$CHCH$_2$ | |
| 81 | " | " | 5-COOC$_2$H$_4$CHCH$_2$ | |
| 82 | " | " | 5-COO-n-C$_8$H$_{16}$CHCH$_2$ | |
| 83 | " | " | 5-COO—CH$_2$CCH | |
| 84 | " | " | 5-COO—C$_2$H$_4$—CCH | |
| 85 | " | " | 5-COO-n-C$_5$H$_{10}$CCH | |
| 86 | " | " | 5-COOCH$_2$Si(CH$_3$)$_3$ | |
| 87 | " | " | 5-COOC$_2$H$_4$OCH$_3$ | |
| 88 | " | " | 5-CONH$_2$ | |
| 89 | " | " | 5-CN | |
| 90 | " | " | 5-CONHCH$_3$ | |
| 91 | 4-Cl | 3-CH$_3$ | 5-CONHC$_2$H$_5$ | |
| 92 | " | " | 5-CONH-n-C$_3$H$_7$ | |
| 93 | " | " | 5-CONH-n-C$_4$H$_9$ | |
| 94 | " | " | 5-CONH-n-C$_6$H$_{13}$ | |
| 95 | " | " | 5-CONH-n-C$_{10}$H$_{21}$ | |
| 96 | " | " | 5-CONH-i-C$_3$H$_7$ | |
| 97 | " | " | 5-CON(CH$_3$)$_2$ | |
| 98 | " | " | 5-CON(CH$_3$)(nC$_6$H$_{13}$) | |
| 99 | " | " | 5-CON(C$_2$H$_5$)$_2$ | |
| 100 | " | " | 5-CO—N(piperidine) | |
| 101 | " | " | 5-CO—N(pyrrolidine) | |
| 102 | " | " | 5-CO—N(morpholine) | |
| 103 | " | " | 5-CO—N(dimethylmorpholine) | |
| 104 | " | " | 5-CO—NH-c-C$_6$H$_{11}$ | |
| 105 | " | " | 5-CO—NH-c-C$_3$H$_5$ | |
| 106 | " | " | 5-CO—N(CH$_3$)(cC$_6$H$_{11}$) | |
| 107 | " | " | 5-COSH | |
| 108 | " | " | 5-COSNa | |
| 109 | " | " | 5-COSCH$_3$ | |
| 110 | " | " | 5-COSC$_2$H$_5$ | |
| 111 | " | " | 5-COSCH$_2$C$_6$H$_5$ | |
| 112 | " | " | 5-COS-nC$_8$H$_{17}$ | |
| 113 | " | " | 5-COSC$_2$H$_4$OCH$_3$ | |
| 114 | " | " | 5-COSCH$_2$CHCH$_2$ | |
| 115 | " | " | 5-COSCH$_2$CCH | |
| 116 | " | " | 5-COS-c-C$_6$H$_{11}$ | |
| 117 | " | " | 5-COSCH$_2$Si(CH$_3$)$_3$ | |
| 118 | " | " | 5-COS-n-C$_4$H$_8$CH(CH$_3$)$_2$ | |
| 119 | " | " | 5-CON(imidazole) | |

TABLE I-continued

Alkyl-aryl-pyrazolecarboxylic acid derivatives

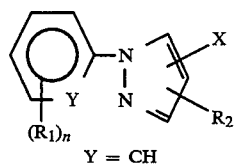

Y = CH (I)

| Example No. | $(R_1)_n$ | $R_2$ | X | Melting point/ boiling point mm Hg [°C.] |
|---|---|---|---|---|
| 120 | " | " | 5-COOC$_2$H$_4$CH(CH$_3$)$_2$ | |
| 121 | 2,4-Cl$_2$ | 5-CH$_3$ | 3-COOCH$_3$ | 87–93 |
| 122 | " | " | 3-COOC$_2$H$_5$ | 78–81 |
| 123 | " | " | 3-COO-n-C$_3$H$_7$ | 99–100 |
| 124 | " | " | 3-COO-i-C$_3$H$_7$ | 65–70 |
| 125 | " | " | 3-COO-n-C$_4$H$_9$ | 76–78 |
| 126 | " | " | 3-COO-n-C$_5$H$_{11}$ | |
| 127 | " | " | 3-COO-n-C$_6$H$_{13}$ | Oil |
| 128 | " | " | 3-COO-n-C$_8$H$_{17}$ | 47–49 |
| 129 | " | " | 3-COO-n-C$_{10}$H$_{21}$ | |
| 130 | " | " | 3-C(=O)-O-C(=O)-[pyrazole-N-N-aryl(R$_1$)$_n$] | 114–117 |
| 131 | " | " | 3-COOH | 112–115 |
| 132 | " | " | 3-COOLi | >250 |
| 133 | " | " | 3-COONa | >250 |
| 134 | " | " | 3-COOK | |
| 135 | " | " | 3-COOCa$_{1/2}$ | 187–188 |
| 136 | " | " | 3-COO-c-C$_4$H$_7$ | |
| 137 | " | " | 3-COO-c-C$_6$H$_{11}$ | 72–74 |
| 138 | " | " | 3-COOCH$_2$—C$_6$H$_5$ | Oil |
| 139 | " | " | 3-COOCH$_2$-(2,4-Cl$_2$—C$_6$H$_3$) | |
| 140 | " | " | 3-COOCH$_2$CHCH$_2$ | Oil |
| 141 | " | " | 3-COOC$_2$H$_4$CHCH$_2$ | |
| 142 | " | " | 3-COO-n-C$_8$H$_{16}$CHCH$_2$ | |
| 143 | " | " | 3-COO—CH$_2$CCH | 101–102 |
| 144 | " | " | 3-COO—C$_2$H$_4$—CCH | |
| 145 | " | " | 3-COO-n-C$_5$H$_{10}$CCH | |
| 146 | " | " | 3-COOCH$_2$Si(CH$_3$)$_3$ | 67–70 |
| 147 | " | " | 3-COOC$_2$H$_4$OCH$_3$ | Oil |
| 148 | " | " | 3-CONH$_2$ | 181 |
| 149 | " | " | 3-CN | |
| 150 | " | " | 3-CONHCH$_3$ | 161–162 |
| 151 | 2,4-Cl$_2$ | 5-CH$_3$ | 3-CONHC$_2$H$_5$ | 87–90 |
| 152 | " | " | 3-CONH-n-C$_3$H$_7$ | 89–92 |
| 153 | " | " | 3-CONH-n-C$_4$H$_9$ | 55–60 |
| 154 | " | " | 3-CONH-n-C$_6$H$_{13}$ | 68–71 |
| 155 | " | " | 3-CONH-n-C$_{10}$H$_{21}$ | |
| 156 | " | " | 3-CONH-i-C$_3$H$_7$ | |
| 157 | " | " | 3-CON(CH$_3$)$_2$ | 99–103 |
| 158 | " | " | 3-CON(CH$_3$)(nC$_6$H$_{13}$) | |
| 159 | " | " | 3-CON(C$_2$H$_5$)$_2$ | Oil |
| 160 | " | " | 3-CO—N(piperidinyl) | Resin |
| 161 | " | " | 3-CO—N(pyrrolidinyl) | |
| 162 | " | " | 3-CO—N(morpholinyl) | Oil |

TABLE I-continued

Alkyl-aryl-pyrazolecarboxylic acid derivatives

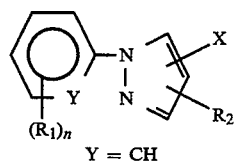

Y = CH (I)

| Example No. | $(R_1)_n$ | $R_2$ | X | Melting point/ boiling point mm Hg [°C.] |
|---|---|---|---|---|
| 163 | " | " | 3-CO—N(morpholine) | Resin |
| 164 | " | " | 3-CO—NH-c-$C_6H_{11}$ | 120–122 |
| 165 | " | " | 3-CO—NH-c-$C_3H_5$ | |
| 166 | " | " | 3-CO—N($CH_3$)(c$C_6H_{11}$) | Oil |
| 167 | " | " | 3-COSH | |
| 168 | " | " | 3-COSNa | |
| 169 | " | " | 3-COS$CH_3$ | |
| 170 | " | " | 3-COS$C_2H_5$ | |
| 171 | " | " | 3-COS$CH_2C_6H_5$ | 70–73 |
| 172 | " | " | 3-COS-n$C_8H_{17}$ | |
| 173 | " | " | 3-COS$C_2H_4OCH_3$ | |
| 174 | " | " | 3-COS$CH_2CHCH_2$ | |
| 175 | " | " | 3-COS$CH_2CCH$ | |
| 176 | " | " | 3-COS-c-$C_6H_{11}$ | |
| 177 | " | " | 3-COS$CH_2Si(CH_3)_3$ | |
| 178 | " | " | 3-COS-n-$C_4H_8CH(CH_3)_2$ | |
| 179 | " | " | 3-CON(imidazole) | |
| 180 | " | " | 3-COO$C_2H_4CH(CH_3)_2$ | |
| 181 | 2,4-$Cl_2$ | 3-$CH_3$ | 5-COO$CH_3$ | |
| 182 | " | " | 5-COO$C_2H_5$ | Oil |
| 183 | " | " | 5-COO-n-$C_3H_7$ | |
| 184 | " | " | 5-COO-i-$C_3H_7$ | |
| 185 | " | " | 5-COO-n-$C_4H_9$ | |
| 186 | " | " | 5-COO-n-$C_5H_{11}$ | |
| 187 | " | " | 5-COO-n-$C_6H_{13}$ | |
| 188 | " | " | 5-COO-n-$C_8H_{17}$ | |
| 189 | " | " | 5-COO-n-$C_{10}H_{21}$ | |
| 190 | " | " | anhydride structure | |
| 191 | " | " | 5-COOH | 195–205 |
| 192 | " | " | 5-COOLi | |
| 193 | " | " | 5-COONa | |
| 194 | " | " | 5-COOK | |
| 195 | " | " | 5-COO$Ca_{1/2}$ | |
| 196 | " | " | 5-COO-c-$C_4H_7$ | |
| 197 | " | " | 5-COO-c-$C_6H_{11}$ | |
| 198 | " | " | 5-COO$CH_2$—$C_6H_5$ | |
| 199 | " | " | 5-COO$CH_2$-(2,4-$Cl_2$—$C_6H_3$) | |
| 200 | " | " | 5-COO$CH_2CHCH_2$ | |
| 201 | " | " | 5-COO$C_2H_4CHCH_2$ | |
| 202 | " | " | 5-COO-n-$C_8H_{16}CHCH_2$ | |
| 203 | " | " | 5-COO—$CH_2CCH$ | |
| 204 | " | " | 5-COO—$C_2H_4$—CCH | |
| 205 | " | " | 5-COO-n-$C_5H_{10}CCH$ | |
| 206 | " | " | 5-COO$CH_2Si(CH_3)_3$ | |
| 207 | " | " | 5-COO$C_2H_4OCH_3$ | |
| 208 | " | " | 5-CON$H_2$ | |
| 209 | " | " | 5-CN | |
| 210 | " | " | 5-CONH$CH_3$ | |

TABLE I-continued
Alkyl-aryl-pyrazolecarboxylic acid derivatives

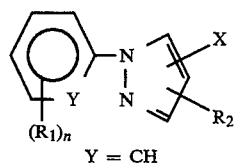

(I)

Y = CH

| Example No. | $(R_1)_n$ | $R_2$ | X | Melting point/ boiling point mm Hg [°C.] |
|---|---|---|---|---|
| 211 | 2,4-Cl$_2$ | 3-CH$_3$ | 5-CONHC$_2$H$_5$ | |
| 212 | " | " | 5-CONH-n-C$_3$H$_7$ | Oil |
| 213 | " | " | 5-CONH-n-C$_4$H$_9$ | |
| 214 | " | " | 5-CONH-n-C$_6$H$_{13}$ | |
| 215 | " | " | 5-CONH-n-C$_{10}$H$_{21}$ | |
| 216 | " | " | 5-CONH-i-C$_3$H$_7$ | |
| 217 | " | " | 5-CON(CH$_3$)$_2$ | |
| 218 | " | " | 5-CON(CH$_3$)(nC$_6$H$_{13}$) | |
| 219 | " | " | 5-CON(C$_2$H$_5$)$_2$ | |
| 220 | " | " | 5-CO—N(piperidinyl) | |
| 221 | " | " | 5-CO—N(pyrrolidinyl) | |
| 222 | " | " | 5-CO—N(morpholinyl) | |
| 223 | " | " | 5-CO—N(2,6-dimethylmorpholinyl) | |
| 224 | " | " | 5-CO—NH-c-C$_6$H$_{11}$ | |
| 225 | " | " | 5-CO—NH-c-C$_3$H$_5$ | |
| 226 | " | " | 5-CO—N(CH$_3$)(cC$_6$H$_{11}$) | |
| 227 | " | " | 5-COSH | |
| 228 | " | " | 5-COSNa | |
| 229 | " | " | 5-COSCH$_3$ | |
| 230 | " | " | 5-COSC$_2$H$_5$ | |
| 231 | " | " | 5-COSCH$_2$C$_6$H$_5$ | |
| 232 | " | " | 5-COS-nC$_8$H$_{17}$ | |
| 233 | " | " | 5-COSC$_2$H$_4$OCH$_3$ | |
| 234 | " | " | 5-COSCH$_2$CHCH$_2$ | |
| 235 | " | " | 5-COSCH$_2$CCH | |
| 236 | " | " | 5-COS-c-C$_6$H$_{11}$ | |
| 237 | " | " | 5-COSCH$_2$Si(CH$_3$)$_3$ | |
| 238 | " | " | 5-COS-n-C$_4$H$_6$CH(CH$_3$)$_2$ | |
| 239 | " | " | 5-CON(imidazolyl) | |
| 240 | " | " | 5-COOC$_2$H$_4$CH(CH$_3$)$_2$ | |
| 241 | 2,4-Cl$_2$ | 5-C$_2$H$_5$ | 3-COOCH$_3$ | |
| 242 | " | " | 3-COOC$_2$H$_5$ | 48–49 |
| 243 | " | " | 3-COO-n-C$_3$H$_7$ | |
| 244 | " | " | 3-COO-i-C$_3$H$_7$ | |
| 245 | " | " | 3-COO-n-C$_4$H$_9$ | |
| 246 | " | " | 3-COO-n-C$_5$H$_{11}$ | |
| 247 | " | " | 3-COO-n-C$_6$H$_{13}$ | |
| 248 | " | " | 3-COO-n-C$_8$H$_{17}$ | |
| 249 | " | " | 3-COO-n-C$_{10}$H$_{21}$ | |

TABLE I-continued
Alkyl-aryl-pyrazolecarboxylic acid derivatives

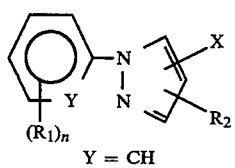

Y = CH (I)

| Example No. | $(R_1)_n$ | $R_2$ | X | Melting point/ boiling point mm Hg [°C.] |
|---|---|---|---|---|
| 250 | " | " | ![structure: 3-C(O)-O-C(O)- linked pyrazole-N-N-aryl $(R_1)_n$, $R_2$, Y] | |
| 251 | " | " | 3-COOH | 193–195 |
| 252 | " | " | 3-COOLi | |
| 253 | " | " | 3-COONa | |
| 254 | " | " | 3-COOK | |
| 255 | " | " | 3-COOCa$_{1/2}$ | |
| 256 | " | " | 3-COO-c-C$_4$H$_7$ | |
| 257 | " | " | 3-COO-c-C$_6$H$_{11}$ | |
| 258 | " | " | 3-COOCH$_2$—C$_6$H$_5$ | |
| 259 | " | " | 3-COOCH$_2$-(2,4-Cl$_2$—C$_6$H$_3$) | |
| 260 | " | " | 3-COOCH$_2$CHCH$_2$ | |
| 261 | " | " | 3-COOC$_2$H$_4$CHCH$_2$ | |
| 262 | " | " | 3-COO-n-C$_8$H$_{16}$CHCH$_2$ | |
| 263 | " | " | 3-COO—CH$_2$CCH | |
| 264 | " | " | 3-COO—C$_2$H$_4$—CCH | |
| 265 | " | " | 3-COO-n-C$_5$H$_{10}$CCH | |
| 266 | " | " | 3-COOCH$_2$Si(CH$_3$)$_3$ | |
| 267 | " | " | 3-COOC$_2$H$_4$OCH$_3$ | |
| 268 | " | " | 3-CONH$_2$ | |
| 269 | " | " | 3-CN | |
| 270 | " | " | 3-CONHCH$_3$ | |
| 271 | 2,4-Cl$_2$ | 5-C$_2$H$_5$ | 3-CONHC$_2$H$_5$ | |
| 272 | " | " | 3-CONH-n-C$_3$H$_7$ | |
| 273 | " | " | 3-CONH-n-C$_4$H$_9$ | |
| 274 | " | " | 3-CONH-n-C$_6$H$_{13}$ | |
| 275 | " | " | 3-CONH-n-C$_{10}$H$_{21}$ | |
| 276 | " | " | 3-CONH-i-C$_3$H$_7$ | |
| 277 | " | " | 3-CON(CH$_3$)$_2$ | |
| 278 | " | " | 3-CON(CH$_3$)(nC$_6$H$_{13}$) | |
| 279 | " | " | 3-CON(C$_2$H$_5$)$_2$ | |
| 280 | " | " | 3-CO—N(piperidinyl) | |
| 281 | " | " | 3-CO—N(pyrrolidinyl) | |
| 282 | " | " | 3-CO—N(morpholinyl) | |
| 283 | " | " | 3-CO—N(2,6-dimethylmorpholinyl) | |
| 284 | " | " | 3-CO—NH-c-C$_6$H$_{11}$ | |
| 285 | " | " | 3-CO—NH-c-C$_3$H$_5$ | |
| 286 | " | " | 3-CO—N(CH$_3$)(cC$_6$H$_{11}$) | |
| 287 | " | " | 3-COSH | |

TABLE I-continued

Alkyl-aryl-pyrazolecarboxylic acid derivatives

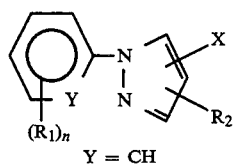

Y = CH (I)

| Example No. | $(R_1)_n$ | $R_2$ | X | Melting point/ boiling point mm Hg [°C.] |
|---|---|---|---|---|
| 288 | " | " | 3-COSNa | |
| 289 | " | " | 3-COSCH$_3$ | |
| 290 | " | " | 3-COSC$_2$H$_5$ | |
| 291 | " | " | 3-COSCH$_2$C$_6$H$_5$ | |
| 292 | " | " | 3-COS-nC$_8$H$_{17}$ | |
| 293 | " | " | 3-COSC$_2$H$_4$OCH$_3$ | |
| 294 | " | " | 3-COSCH$_2$CHCH$_2$ | |
| 295 | " | " | 3-COSCH$_2$CCH | |
| 296 | " | " | 3-COS-c-C$_6$H$_{11}$ | |
| 297 | " | " | 3-COSCH$_2$Si(CH$_3$)$_3$ | |
| 298 | " | " | 3-COS-n-C$_4$H$_8$CH(CH$_3$)$_2$ | |
| 299 | " | " | 3-CON⟨imidazolyl⟩ | |
| 300 | " | " | 3-COOC$_2$H$_4$CH(CH$_3$)$_2$ | |
| 301 | 2,4-Cl$_2$ | 5-CH(CH$_3$)$_2$ | 3-COOCH$_3$ | 144 |
| 302 | " | " | 3-COOC$_2$H$_5$ | 70–77 |
| 303 | " | " | 3-COO-n-C$_3$H$_7$ | Öl |
| 304 | " | " | 3-COO-i-C$_3$H$_7$ | Öl |
| 305 | " | " | 3-COO-n-C$_4$H$_9$ | |
| 306 | " | " | 3-COO-n-C$_5$H$_{11}$ | |
| 307 | " | " | 3-COO-n-C$_6$H$_{13}$ | |
| 308 | " | " | 3-COO-n-C$_8$H$_{17}$ | |
| 309 | " | " | 3-COO-n-C$_{10}$H$_{21}$ | |
| 310 | " | " | [anhydride structure] | |
| 311 | " | " | 3-COOH | 195–196 |
| 312 | " | " | 3-COOLi | |
| 313 | " | " | 3-COONa | >250 |
| 314 | " | " | 3-COOK | |
| 315 | " | " | 3-COOCa$_{1/2}$ | |
| 316 | " | " | 3-COO-c-C$_4$H$_7$ | |
| 317 | " | " | 3-COO-c-C$_6$H$_{11}$ | |
| 318 | " | " | 3-COOCH$_2$—C$_6$H$_5$ | |
| 319 | " | " | 3-COOCH$_2$-(2,4-Cl$_2$—C$_6$H$_3$) | |
| 320 | " | " | 3-COOCH$_2$CHCH$_2$ | |
| 321 | " | " | 3-COOC$_2$H$_4$CHCH$_2$ | |
| 322 | " | " | 3-COO-n-C$_8$H$_{16}$CHCH$_2$ | |
| 323 | " | " | 3-COO—CH$_2$CCH | |
| 324 | " | " | 3-COO—C$_2$H$_4$—CCH | |
| 325 | " | " | 3-COO-n-C$_5$H$_{10}$CCH | |
| 326 | " | " | 3-COOCH$_2$Si(CH$_3$)$_3$ | |
| 327 | " | " | 3-COOC$_2$H$_4$OCH$_3$ | |
| 328 | " | " | 3-CONH$_2$ | |
| 329 | " | " | 3-CN | |
| 330 | " | " | 3-CONHCH$_3$ | |
| 331 | 2,4-Cl$_2$ | 5-CH(CH$_3$)$_2$ | 3-CONHC$_2$H$_5$ | 106–109 |
| 332 | " | " | 3-CONH-n-C$_3$H$_7$ | 67 |
| 333 | " | " | 3-CONH-n-C$_4$H$_9$ | |
| 334 | " | " | 3-CONH-n-C$_6$H$_{13}$ | |
| 335 | " | " | 3-CONH-n-C$_{10}$H$_{21}$ | |
| 336 | " | " | 3-CONH-i-C$_3$H$_7$ | |
| 337 | " | " | 3-CON(CH$_3$)$_2$ | |
| 338 | " | " | 3-CON(CH$_3$)(nC$_6$H$_{13}$) | |
| 339 | " | " | 3-CON(C$_2$H$_5$)$_2$ | 98–100 |

TABLE I-continued

Alkyl-aryl-pyrazolecarboxylic acid derivatives

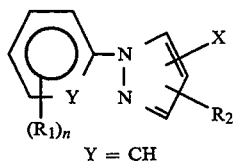

Y = CH

| Example No. | (R₁)ₙ | R₂ | X | Melting point/ boiling point mm Hg [°C.] |
|---|---|---|---|---|
| 340 | " | " | 3-CO—N(piperidinyl) | |
| 341 | " | " | 3-CO—N(pyrrolidinyl) | |
| 342 | " | " | 3-CO—N(morpholinyl) | |
| 343 | " | " | 3-CO—N(2,6-dimethylmorpholinyl) | 140–142 |
| 344 | " | " | 3-CO—NH-c-C₆H₁₁ | |
| 345 | " | " | 3-CO—NH-c-C₃H₅ | |
| 346 | " | " | 3-CO—N(CH₃)(cC₆H₁₁) | |
| 347 | " | " | 3-COSH | |
| 348 | " | " | 3-COSNa | |
| 349 | " | " | 3-COSCH₃ | |
| 350 | " | " | 3-COSC₂H₅ | |
| 351 | " | " | 3-COSCH₂C₆H₅ | |
| 352 | " | " | 3-COS-nC₈H₁₇ | |
| 353 | " | " | 3-COSC₂H₄OCH₃ | |
| 354 | " | " | 3-COSCH₂CHCH₂ | |
| 355 | " | " | 3-COSCH₂CCH | |
| 356 | " | " | 3-COS-c-C₆H₁₁ | |
| 357 | " | " | 3-COSCH₂Si(CH₃)₃ | |
| 358 | " | " | 3-COS-n-C₄H₆CH(CH₃)₂ | |
| 359 | " | " | 3-CON(imidazolyl) | |
| 360 | " | " | 3-COOC₂H₄CH(CH₃)₂ | |
| 361 | 2,4-Cl₂ | 5-C(CH₃)₃ | 3-COOCH₃ | Resin |
| 362 | " | " | 3-COOC₂H₅ | 118–121 |
| 363 | " | " | 3-COO-n-C₃H₇ | |
| 364 | " | " | 3-COO-i-C₃H₇ | |
| 365 | " | " | 3-COO-n-C₄H₉ | |
| 366 | " | " | 3-COO-n-C₅H₁₁ | |
| 367 | " | " | 3-COO-n-C₆H₁₃ | |
| 368 | " | " | 3-COO-n-C₈H₁₇ | |
| 369 | " | " | 3-COO-n-C₁₀H₂₁ | |
| 370 | " | " | (anhydride dimer structure) | |
| 371 | " | " | 3-COOH | |
| 372 | " | " | 3-COOLi | |

TABLE I-continued

Alkyl-aryl-pyrazolecarboxylic acid derivatives

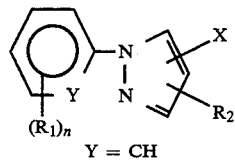

Y = CH

| Example No. | $(R_1)_n$ | $R_2$ | X | Melting point/ boiling point mm Hg [°C.] |
|---|---|---|---|---|
| 373 | " | " | 3-COONa | |
| 374 | " | " | 3-COOK | |
| 375 | " | " | 3-COOCa$_{1/2}$ | |
| 376 | " | " | 3-COO-c-C$_4$H$_7$ | |
| 377 | " | " | 3-COO-c-C$_6$H$_{11}$ | |
| 378 | " | " | 3-COOCH$_2$—C$_6$H$_5$ | |
| 379 | " | " | 3-COOCH$_2$-(2,4-Cl$_2$—C$_6$H$_3$) | |
| 380 | " | " | 3-COOCH$_2$CHCH$_2$ | |
| 381 | " | " | 3-COOC$_2$H$_4$CHCH$_2$ | |
| 382 | " | " | 3-COO-n-C$_8$H$_{16}$CHCH$_2$ | |
| 383 | " | " | 3-COO—CH$_2$CCH | |
| 384 | " | " | 3-COO—C$_2$H$_4$—CCH | |
| 385 | " | " | 3-COO-n-C$_5$H$_{10}$CCH | |
| 386 | " | " | 3-COOCH$_2$Si(CH$_3$)$_3$ | |
| 387 | " | " | 3-COOC$_2$H$_4$OCH$_3$ | |
| 388 | " | " | 3-CONH$_2$ | |
| 389 | " | " | 3-CN | |
| 390 | " | " | 3-CONHCH$_3$ | |
| 391 | 2,4-Cl$_2$ | 5-C(CH$_3$)$_3$ | 3-CONHC$_2$H$_5$ | 161–162 |
| 392 | " | " | 3-CONH-n-C$_3$H$_7$ | 102–103 |
| 393 | " | " | 3-CONH-n-C$_4$H$_9$ | |
| 394 | " | " | 3-CONH-n-C$_6$H$_{13}$ | |
| 395 | " | " | 3-CONH-n-C$_{10}$H$_{21}$ | |
| 396 | " | " | 3-CONH-i-C$_3$H$_7$ | |
| 397 | " | " | 3-CON(CH$_3$)$_2$ | |
| 398 | " | " | 3-CON(CH$_3$)(nC$_6$H$_{13}$) | |
| 399 | " | " | 3-CON(C$_2$H$_5$)$_2$ | |
| 400 | " | " | 3-CO—N(piperidinyl) | |
| 401 | " | " | 3-CO—N(pyrrolidinyl) | |
| 402 | " | " | 3-CO—N(morpholinyl) | |
| 403 | " | " | 3-CO—N(2,6-dimethylmorpholinyl) | |
| 404 | " | " | 3-CO—NH-c-C$_6$H$_{11}$ | |
| 405 | " | " | 3-CO—NH-c-C$_3$H$_5$ | |
| 406 | " | " | 3-CO—N(CH$_3$)(cC$_6$H$_{11}$) | |
| 407 | " | " | 3-COSH | |
| 408 | " | " | 3-COSNa | |
| 409 | " | " | 3-COSCH$_3$ | |
| 410 | " | " | 3-COSC$_2$H$_5$ | |
| 411 | " | " | 3-COSCH$_2$C$_6$H$_5$ | |
| 412 | " | " | 3-COS-nC$_8$H$_{17}$ | |
| 413 | " | " | 3-COSC$_2$H$_4$OCH$_3$ | |
| 414 | " | " | 3-COSCH$_2$CHCH$_2$ | |
| 415 | " | " | 3-COSCH$_2$CCH | |
| 416 | " | " | 3-COS-c-C$_6$H$_{11}$ | |
| 417 | " | " | 3-COSCH$_2$Si(CH$_3$)$_3$ | |
| 418 | " | " | 3-COS-n-C$_4$H$_8$CH(CH$_3$)$_2$ | |

TABLE I-continued

Alkyl-aryl-pyrazolecarboxylic acid derivatives (I)

Y = CH

| Example No. | $(R_1)_n$ | $R_2$ | X | Melting point/ boiling point mm Hg [°C.] |
|---|---|---|---|---|
| 419 | " | " | 3-CON(imidazolyl) | |
| 420 | " | " | 3-COOC$_2$H$_4$CH(CH$_3$)$_2$ | |
| 421 | 2,4-Cl$_2$ | 5-CH$_2$—CH(CH$_3$)$_2$ | 3-COOCH$_3$ | |
| 422 | " | " | 3-COOC$_2$H$_5$ | Oil |
| 423 | " | " | 3-COO-n-C$_3$H$_7$ | |
| 424 | " | " | 3-COO-i-C$_3$H$_7$ | |
| 425 | " | " | 3-COO-n-C$_4$H$_9$ | |
| 426 | " | " | 3-COO-n-C$_5$H$_{11}$ | |
| 427 | " | " | 3-COO-n-C$_6$H$_{13}$ | |
| 428 | " | " | 3-COO-n-C$_8$H$_{17}$ | |
| 429 | " | " | 3-COO-n-C$_{10}$H$_{21}$ | |
| 430 | " | " | 3-C(O)-O-C(O)-(pyrazole-aryl) | |
| 431 | " | " | 3-COOH | |
| 432 | " | " | 3-COOLi | |
| 433 | " | " | 3-COONa | |
| 434 | " | " | 3-COOK | |
| 435 | " | " | 3-COOCa$_{1/2}$ | |
| 436 | " | " | 3-COO-c-C$_4$H$_7$ | |
| 437 | " | " | 3-COO-c-C$_6$H$_{11}$ | |
| 438 | " | " | 3-COOCH$_2$—C$_6$H$_5$ | |
| 439 | " | " | 3-COOCH$_2$-(2,4-Cl$_2$—C$_6$H$_3$) | |
| 440 | " | " | 3-COOCH$_2$CHCH$_2$ | |
| 441 | " | " | 3-COOC$_2$H$_4$CHCH$_2$ | |
| 442 | " | " | 3-COO-n-C$_8$H$_{16}$CHCH$_2$ | |
| 443 | " | " | 3-COO—CH$_2$CCH | |
| 444 | " | " | 3-COO—C$_2$H$_4$—CCH | |
| 445 | " | " | 3-COO-n-C$_5$H$_{10}$CCH | |
| 446 | " | " | 3-COOCH$_2$Si(CH$_3$)$_3$ | |
| 447 | " | " | 3-COOC$_2$H$_4$OCH$_3$ | |
| 448 | " | " | 3-CONH$_2$ | |
| 449 | " | " | 3-CN | |
| 450 | " | " | 3-CONHCH$_3$ | |
| 451 | 2,4-Cl$_2$ | 5-CH$_2$CH(CH$_2$)$_3$ | 3-CONHC$_2$H$_5$ | |
| 452 | " | " | 3-CONH-n-C$_3$H$_7$ | |
| 453 | " | " | 3-CONH-n-C$_4$H$_9$ | |
| 454 | " | " | 3-CONH-n-C$_6$H$_{13}$ | |
| 455 | " | " | 3-CONH-n-C$_{10}$H$_{21}$ | |
| 456 | " | " | 3-CONH-i-C$_3$H$_7$ | |
| 457 | " | " | 3-CON(CH$_3$)$_2$ | |
| 458 | " | " | 3-CON(CH$_3$)(nC$_6$H$_{13}$) | |
| 459 | " | " | 3-CON(C$_2$H$_5$)$_2$ | |
| 460 | " | " | 3-CO—N(piperidinyl) | |
| 461 | " | " | 3-CO—N(pyrrolidinyl) | |

TABLE I-continued
Alkyl-aryl-pyrazolecarboxylic acid derivatives

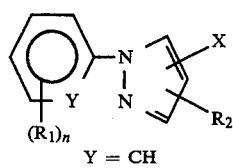

Y = CH

| Example No. | (R$_1$)$_n$ | R$_2$ | X | Melting point/ boiling point mm Hg [°C.] |
|---|---|---|---|---|
| 462 | " | " | 3-CO—N⌒O (morpholine) | |
| 463 | " | " | 3-CO—N⌒O (dimethylmorpholine) | |
| 464 | " | " | 3-CO—NH-c-C$_6$H$_{11}$ | |
| 465 | " | " | 3-CO—NH-c-C$_3$H$_5$ | |
| 466 | " | " | 3-CO—N(CH$_3$)(cC$_6$H$_{11}$) | |
| 467 | " | " | 3-COSH | |
| 468 | " | " | 3-COSNa | |
| 469 | " | " | 3-COSCH$_3$ | |
| 470 | " | " | 3-COSC$_2$H$_5$ | |
| 471 | " | " | 3-COSCH$_2$C$_6$H$_5$ | |
| 472 | " | " | 3-COS-nC$_8$H$_{17}$ | |
| 473 | " | " | 3-COSC$_2$H$_4$OCH$_3$ | |
| 474 | " | " | 3-COSCH$_2$CHCH$_2$ | |
| 475 | " | " | 3-COSCH$_2$CCH | |
| 476 | " | " | 3-COS-c-C$_6$H$_{11}$ | |
| 477 | " | " | 3-COSCH$_2$Si(CH$_3$)$_3$ | |
| 478 | " | " | 3-COS-n-C$_4$H$_8$CH(CH$_3$)$_2$ | |
| 479 | " | " | 3-CON⌒(imidazole) | |
| 480 | " | " | 3-COOC$_2$H$_4$CH(CH$_3$)$_2$ | |
| 481 | 2,4-Cl$_2$ | 5-c-C$_6$H$_{11}$ | 3-COOCH$_3$ | |
| 482 | " | " | 3-COOC$_2$H$_5$ | 106–108 |
| 483 | " | " | 3-COO-n-C$_3$H$_7$ | |
| 484 | " | " | 3-COO-i-C$_3$H$_7$ | |
| 485 | " | " | 3-COO-n-C$_4$H$_9$ | |
| 486 | " | " | 3-COO-n-C$_5$H$_{11}$ | |
| 487 | " | " | 3-COO-n-C$_6$H$_{13}$ | |
| 488 | " | " | 3-COO-n-C$_8$H$_{17}$ | |
| 489 | " | " | 3-COO-n-C$_{10}$H$_{21}$ | |
| 490 | " | " | (anhydride structure) | |
| 491 | " | " | 3-COOH | 201–202 |
| 492 | " | " | 3-COOLi | |
| 493 | " | " | 3-COONa | |
| 494 | " | " | 3-COOK | |
| 495 | " | " | 3-COOCa$_{1/2}$ | |
| 496 | " | " | 3-COO-c-C$_4$H$_7$ | |
| 497 | " | " | 3-COO-c-C$_6$H$_{11}$ | |
| 498 | " | " | 3-COOCH$_2$—C$_6$H$_5$ | |
| 499 | " | " | 3-COOCH$_2$-(2,4-Cl$_2$—C$_6$H$_3$) | |
| 500 | " | " | 3-COOCH$_2$CHCH$_2$ | |
| 501 | " | " | 3-COOC$_2$H$_4$CHCH$_2$ | |
| 502 | " | " | 3-COO-n-C$_8$H$_{16}$CHCH$_2$ | |
| 503 | " | " | 3-COO—CH$_2$CCH | |
| 504 | " | " | 3-COO—C$_2$H$_4$—CCH | |

TABLE I-continued

Alkyl-aryl-pyrazolecarboxylic acid derivatives

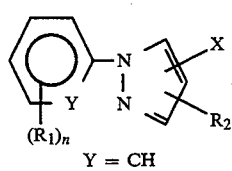

Y = CH

| Example No. | (R₁)ₙ | R₂ | X | Melting point/ boiling point mm Hg [°C.] |
|---|---|---|---|---|
| 505 | " | " | 3-COO-n-C₅H₁₀CCH | |
| 506 | " | " | 3-COOCH₂Si(CH₃)₃ | |
| 507 | " | " | 3-COOC₂H₄OCH₃ | |
| 508 | " | " | 3-CONH₂ | |
| 509 | " | " | 3-CN | |
| 510 | " | " | 3-CONHCH₃ | |
| 511 | 2,4-Cl₂ | 5-c-C₆H₁₁ | 3-CONHC₂H₅ | 131–132 |
| 512 | " | " | 3-CONH-n-C₃H₇ | |
| 513 | " | " | 3-CONH-n-C₄H₉ | |
| 514 | " | " | 3-CONH-n-C₆H₁₃ | |
| 515 | " | " | 3-CONH-n-C₁₀H₂₁ | |
| 516 | " | " | 3-CONH-i-C₃H₇ | |
| 517 | " | " | 3-CON(CH₃)₂ | |
| 518 | " | " | 3-CON(CH₃)(nC₆H₁₃) | |
| 519 | " | " | 3-CON(C₂H₅)₂ | |
| 520 | " | " | 3-CO—N(piperidinyl) | |
| 521 | " | " | 3-CO—N(pyrrolidinyl) | |
| 522 | " | " | 3-CO—N(morpholinyl) | |
| 523 | " | " | 3-CO—N(2,6-dimethylmorpholinyl) | |
| 524 | " | " | 3-CO—NH-c-C₆H₁₁ | |
| 525 | " | " | 3-CO—NH-c-C₃H₅ | |
| 526 | " | " | 3-CO—N(CH₃)(cC₆H₁₁) | |
| 527 | " | " | 3-COSH | |
| 528 | " | " | 3-COSNa | |
| 529 | " | " | 3-COSCH₃ | |
| 530 | " | " | 3-COSC₂H₅ | |
| 531 | " | " | 3-COSCH₂C₆H₅ | |
| 532 | " | " | 3-COS-nC₈H₁₇ | |
| 533 | " | " | 3-COSC₂H₄OCH₃ | |
| 534 | " | " | 3-COSCH₂CHCH₂ | |
| 535 | " | " | 3-COSCH₂CCH | |
| 536 | " | " | 3-COS-c-C₆H₁₁ | |
| 537 | " | " | 3-COSCH₂Si(CH₃)₃ | |
| 538 | " | " | 3-COS-n-C₄H₈CH(CH₃)₂ | |
| 539 | " | " | 3-CON(imidazolyl) | |
| 540 | " | " | 3-COOC₂H₄CH(CH₃)₂ | |
| 541 | 2,4-Br₂ | 5-CH₃ | 3-COOCH₃ | |
| 542 | " | " | 3-COOC₂H₅ | 91–100 |
| 543 | " | " | 3-COO-n-C₃H₇ | |

TABLE I-continued

Alkyl-aryl-pyrazolecarboxylic acid derivatives

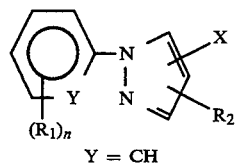

Y = CH (I)

| Example No. | $(R_1)_n$ | $R_2$ | X | Melting point/ boiling point mm Hg [°C.] |
|---|---|---|---|---|
| 544 | " | " | 3-COO-i-$C_3H_7$ | |
| 545 | " | " | 3-COO-n-$C_4H_9$ | |
| 546 | " | " | 3-COO-n-$C_5H_{11}$ | |
| 547 | " | " | 3-COO-n-$C_6H_{13}$ | |
| 548 | " | " | 3-COO-n-$C_8H_{17}$ | |
| 549 | " | " | 3-COO-n-$C_{10}H_{21}$ | |
| 550 | " | " | ![anhydride structure with 3-C(=O)-O-C(=O)- linked to pyrazole with R_2, N-N, aryl (R_1)_n, Y] | |
| 551 | " | " | 3-COOH | |
| 552 | " | " | 3-COOLi | |
| 553 | " | " | 3-COONa | |
| 554 | " | " | 3-COOK | |
| 555 | " | " | 3-COOCa$_{1/2}$ | |
| 556 | " | " | 3-COO-c-$C_4H_7$ | |
| 557 | " | " | 3-COO-c-$C_6H_{11}$ | |
| 558 | " | " | 3-COOCH$_2$—$C_6H_5$ | |
| 559 | " | " | 3-COOCH$_2$-(2,4-Cl$_2$—$C_6H_3$) | |
| 560 | " | " | 3-COOCH$_2$CHCH$_2$ | |
| 561 | " | " | 3-COOC$_2$H$_4$CHCH$_2$ | |
| 562 | " | " | 3-COO-n-$C_8H_{16}$CHCH$_2$ | |
| 563 | " | " | 3-COO—CH$_2$CCH | |
| 564 | " | " | 3-COO—C$_2$H$_4$—CCH | |
| 565 | " | " | 3-COO-n-$C_5H_{10}$CCH | |
| 566 | " | " | 3-COOCH$_2$Si(CH$_3$)$_3$ | |
| 567 | " | " | 3-COOC$_2$H$_4$OCH$_3$ | |
| 568 | " | " | 3-CONH$_2$ | |
| 569 | " | " | 3-CN | |
| 570 | " | " | 3-CONHCH$_3$ | |
| 571 | 2,4-Br$_2$ | 5-CH$_3$ | 3-CONHC$_2$H$_5$ | |
| 572 | " | " | 3-CONH-n-$C_3H_7$ | |
| 573 | " | " | 3-CONH-n-$C_4H_9$ | |
| 574 | " | " | 3-CONH-n-$C_6H_{13}$ | |
| 575 | " | " | 3-CONH-n-$C_{10}H_{21}$ | |
| 576 | " | " | 3-CONH-i-$C_3H_7$ | |
| 577 | " | " | 3-CON(CH$_3$)$_2$ | |
| 578 | " | " | 3-CON(CH$_3$)(nC$_6$H$_{13}$) | |
| 579 | " | " | 3-CON(C$_2$H$_5$)$_2$ | |
| 580 | " | " | 3-CO—N(piperidinyl) | |
| 581 | " | " | 3-CO—N(pyrrolidinyl) | |
| 582 | " | " | 3-CO—N(morpholinyl) | |

TABLE I-continued

Alkyl-aryl-pyrazolecarboxylic acid derivatives

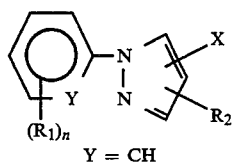

Y = CH (I)

| Example No. | $(R_1)_n$ | $R_2$ | X | Melting point/ boiling point mm Hg [°C.] |
|---|---|---|---|---|
| 583 | " | " | 3-CO—N(morpholino) | |
| 584 | " | " | 3-CO—NH-c-$C_6H_{11}$ | |
| 585 | " | " | 3-CO—NH-c-$C_3H_5$ | |
| 586 | " | " | 3-CO—N($CH_3$)(c$C_6H_{11}$) | |
| 587 | " | " | 3-COSH | |
| 588 | " | " | 3-COSNa | |
| 589 | " | " | 3-COS$CH_3$ | |
| 590 | " | " | 3-COS$C_2H_5$ | |
| 591 | " | " | 3-COS$CH_2C_6H_5$ | |
| 592 | " | " | 3-COS-n$C_8H_{17}$ | |
| 593 | " | " | 3-COS$C_2H_4OCH_3$ | |
| 594 | " | " | 3-COS$CH_2CHCH_2$ | |
| 595 | " | " | 3-COS$CH_2CCH$ | |
| 596 | " | " | 3-COS-c-$C_6H_{11}$ | |
| 597 | " | " | 3-COS$CH_2Si(CH_3)_3$ | |
| 598 | " | " | 3-COS-n-$C_4H_8CH(CH_3)_2$ | |
| 599 | " | " | 3-CON(imidazolyl) | |
| 600 | " | " | 3-COO$C_2H_4CH(CH_3)_2$ | |
| 601 | 3-$CF_3$ | 5-$CH_3$ | 3-COO$CH_3$ | |
| 602 | " | " | 3-COO$C_2H_5$ | 73–75 |
| 603 | " | " | 3-COO-n-$C_3H_7$ | |
| 604 | " | " | 3-COO-i-$C_3H_7$ | |
| 605 | " | " | 3-COO-n-$C_4H_9$ | Öl |
| 606 | " | " | 3-COO-n-$C_5H_{11}$ | |
| 607 | " | " | 3-COO-n-$C_6H_{13}$ | |
| 608 | " | " | 3-COO-n-$C_8H_{17}$ | |
| 609 | " | " | 3-COO-n-$C_{10}H_{21}$ | |
| 610 | " | " | anhydride dimer | |
| 611 | " | " | 3-COOH | 190–191 |
| 612 | " | " | 3-COOLi | |
| 613 | " | " | 3-COONa | |
| 614 | " | " | 3-COOK | |
| 615 | " | " | 3-COO$Ca_{1/2}$ | |
| 616 | " | " | 3-COO-c-$C_4H_7$ | |
| 617 | " | " | 3-COO-c-$C_6H_{11}$ | |
| 618 | " | " | 3-COO$CH_2$—$C_6H_5$ | |
| 619 | " | " | 3-COO$CH_2$-(2,4-$Cl_2$—$C_6H_3$) | |
| 620 | " | " | 3-COO$CH_2CHCH_2$ | |
| 621 | " | " | 3-COO$C_2H_4CHCH_2$ | |
| 622 | " | " | 3-COO-n-$C_8H_{16}CHCH_2$ | |
| 623 | " | " | 3-COO—$CH_2CCH$ | |
| 624 | " | " | 3-COO—$C_2H_4$—CCH | |
| 625 | " | " | 3-COO-n-$C_5H_{10}CCH$ | |
| 626 | " | " | 3-COO$CH_2Si(CH_3)_3$ | |
| 627 | " | " | 3-COO$C_2H_4OCH_3$ | |
| 628 | " | " | 3-CON$H_2$ | |
| 629 | " | " | 3-CN | |
| 630 | " | " | 3-CONH$CH_3$ | |

TABLE I-continued

Alkyl-aryl-pyrazolecarboxylic acid derivatives

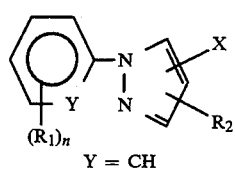

Y = CH

| Example No. | $(R_1)_n$ | $R_2$ | X | Melting point/ boiling point mm Hg [°C.] |
|---|---|---|---|---|
| 631 | 3-CF$_3$ | 5-CH$_3$ | 3-CONHC$_2$H$_5$ | |
| 632 | " | " | 3-CONH-n-C$_3$H$_7$ | 66–72 |
| 633 | " | " | 3-CONH-n-C$_4$H$_9$ | |
| 634 | " | " | 3-CONH-n-C$_6$H$_{13}$ | |
| 635 | " | " | 3-CONH-n-C$_{10}$H$_{21}$ | |
| 636 | " | " | 3-CONH-i-C$_3$H$_7$ | |
| 637 | " | " | 3-CON(CH$_3$)$_2$ | |
| 638 | " | " | 3-CON(CH$_3$)(nC$_6$H$_{13}$) | |
| 639 | " | " | 3-CON(C$_2$H$_5$)$_2$ | |
| 640 | " | " | 3-CO—N(piperidinyl) | |
| 641 | " | " | 3-CO—N(pyrrolidinyl) | |
| 642 | " | " | 3-CO—N(morpholinyl) | |
| 643 | " | " | 3-CO—N(2,6-dimethylmorpholinyl) | |
| 644 | " | " | 3-CO—NH-c-C$_6$H$_{11}$ | |
| 645 | " | " | 3-CO—NH-c-C$_3$H$_5$ | |
| 646 | " | " | 3-CO—N(CH$_3$)(cC$_6$H$_{11}$) | |
| 647 | " | " | 3-COSH | |
| 648 | " | " | 3-COSNa | |
| 649 | " | " | 3-COSCH$_3$ | |
| 650 | " | " | 3-COSC$_2$H$_5$ | |
| 651 | " | " | 3-COSCH$_2$C$_6$H$_5$ | |
| 652 | " | " | 3-COS-nC$_8$H$_{17}$ | |
| 653 | " | " | 3-COSC$_2$H$_4$OCH$_3$ | |
| 654 | " | " | 3-COSCH$_2$CHCH$_2$ | |
| 655 | " | " | 3-COSCH$_2$CCH | |
| 656 | " | " | 3-COS-c-C$_6$H$_{11}$ | |
| 657 | " | " | 3-COSCH$_2$Si(CH$_3$)$_3$ | |
| 658 | " | " | 3-COS-n-C$_4$H$_8$CH(CH$_3$)$_2$ | |
| 659 | " | " | 3-CON(imidazolyl) | |
| 660 | " | " | 3-COOC$_2$H$_4$CH(CH$_3$)$_2$ | |
| 661 | 2,4-ClCF$_3$ | 5-CH$_3$ | 3-CONHC$_2$H$_5$ | |
| 662 | " | " | 3-CONH-n-C$_3$H$_7$ | 109–113 |
| 663 | " | " | 3-CONH-n-C$_4$H$_9$ | |
| 664 | " | " | 3-CONH-n-C$_6$H$_{13}$ | |
| 665 | " | " | 3-CONH-n-C$_{10}$H$_{21}$ | |
| 666 | " | " | 3-COHN-i-C$_3$H$_7$ | |
| 667 | " | " | 3-CON(CH$_3$)$_2$ | |
| 668 | " | " | 3-CON(CH$_3$)(nC$_6$H$_{13}$) | |
| 669 | " | " | 3-CON(C$_2$H$_5$)$_2$ | |

TABLE I-continued
Alkyl-aryl-pyrazolecarboxylic acid derivatives

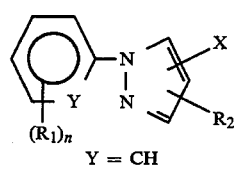

(I)

Y = CH

| Example No. | $(R_1)_n$ | $R_2$ | X | Melting point/ boiling point mm Hg [°C.] |
|---|---|---|---|---|
| 670 | " | " | 3-CO—N(piperidinyl) | |
| 671 | " | " | 3-CO—N(pyrrolidinyl) | |
| 672 | " | " | 3-CO—N(morpholinyl) | |
| 673 | " | " | 3-CO—N(2,6-dimethylmorpholinyl) | |
| 674 | " | " | 3-CO—NH-c-$C_6H_{11}$ | |
| 675 | " | " | 3-CO—NH-c-$C_3H_5$ | |
| 676 | " | " | 3-CO—N($CH_3$)(c$C_6H_{11}$) | |
| 677 | " | " | 3-COSH | |
| 678 | " | " | 3-COSNa | |
| 679 | " | " | 3-COS$CH_3$ | |
| 680 | " | " | 3-COS$C_2H_5$ | |
| 681 | " | " | 3-COS$CH_2C_6H_5$ | |
| 682 | " | " | 3-COS-n$C_8H_{17}$ | |
| 683 | " | " | 3-COS$C_2H_4OCH_3$ | |
| 684 | " | " | 3-COS$CH_2CHCH_2$ | |
| 685 | " | " | 3-COS$CH_2CCH$ | |
| 686 | " | " | 3-COS-c-$C_6H_{11}$ | |
| 687 | " | " | 3-COS$CH_2Si(CH_3)_3$ | |
| 688 | " | " | 3-COS-n-$C_4H_8CH(CH_3)_2$ | |
| 689 | " | " | 3-CON(imidazolyl) | |
| 690 | " | " | 3-COO$C_2H_4CH(CH_3)_2$ | |
| 691 | 2,4-Cl$CF_3$ | 5-$CH_3$ | 3-COO$CH_3$ | |
| 692 | " | " | 3-COO$C_2H_5$ | |
| 693 | " | " | 3-COO-n-$C_3H_7$ | |
| 694 | " | " | 3-COO-i-$C_3H_7$ | |
| 695 | " | " | 3-COO-n-$C_4H_9$ | |
| 696 | " | " | 3-COO-n-$C_5H_{11}$ | |
| 697 | " | " | 3-COO-n-$C_6H_{13}$ | |
| 698 | " | " | 3-COO-n-$C_8H_{17}$ | |
| 699 | " | " | 3-COO-n-$C_{10}H_{21}$ | |
| 700 | " | " | 3-C(O)-O-C(O)-pyrazole-aryl anhydride structure | |
| 701 | " | " | 3-COOH | |

TABLE I-continued

Alkyl-aryl-pyrazolecarboxylic acid derivatives

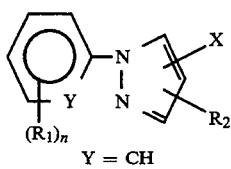

Y = CH (I)

| Example No. | $(R_1)_n$ | $R_2$ | X | Melting point/ boiling point mm Hg [°C.] |
|---|---|---|---|---|
| 702 | " | " | 3-COOLi | |
| 703 | " | " | 3-COONa | |
| 704 | " | " | 3-COOK | |
| 705 | " | " | 3-COOCa$_{1/2}$ | |
| 706 | " | " | 3-COO-c-$C_4H_7$ | |
| 707 | " | " | 3-COO-c-$C_6H_{11}$ | |
| 708 | " | " | 3-COOCH$_2$—$C_6H_5$ | |
| 709 | " | " | 3-COOCH$_2$-(2,4-Cl$_2$—$C_6H_3$) | |
| 710 | " | " | 3-COOCH$_2$CHCH$_2$ | |
| 711 | " | " | 3-COOC$_2$H$_4$CHCH$_2$ | |
| 712 | " | " | 3-COO-n-C$_8$H$_{16}$CHCH$_2$ | |
| 713 | " | " | 3-COO—CH$_2$CCH | |
| 714 | " | " | 3-COO—C$_2$H$_4$—CCH | |
| 715 | " | " | 3-COO-n-C$_5$H$_{10}$CCH | |
| 716 | " | " | 3-COOCH$_2$Si(CH$_3$)$_3$ | |
| 717 | " | " | 3-COOC$_2$H$_4$OCH$_3$ | |
| 718 | " | " | 3-CONH$_2$ | |
| 719 | " | " | 3-CN | |
| 720 | " | " | 3-CONHCH$_3$ | |
| 721 | 4,2-ClCF$_3$ | 5-CH$_3$ | 3-COOCH$_3$ | |
| 722 | " | " | 3-COOC$_2$H$_5$ | 49–51 |
| 723 | " | " | 3-COO-n-C$_3$H$_7$ | |
| 724 | " | " | 3-COO-i-C$_3$H$_7$ | |
| 725 | " | " | 3-COO-n-C$_4$H$_9$ | |
| 726 | " | " | 3-COO-n-C$_5$H$_{11}$ | |
| 727 | " | " | 3-COO-n-C$_6$H$_{13}$ | |
| 728 | " | " | 3-COO-n-C$_8$H$_{17}$ | |
| 729 | " | " | 3-COO-n-C$_{10}$H$_{21}$ | |

730 " "

[structure showing: 3-C(=O)-O-C(=O)- pyrazole with $R_2$, N-N linked to phenyl with $(R_1)_n$ and Y]

| 731 | " | " | 3-COOH | |
| 732 | " | " | 3-COOLi | |
| 733 | " | " | 3-COONa | |
| 734 | " | " | 3-COOK | |
| 735 | " | " | 3-COOCa$_{1/2}$ | |
| 736 | " | " | 3-COO-c-C$_4$H$_7$ | |
| 737 | " | " | 3-COO-c-C$_6$H$_{11}$ | |
| 738 | " | " | 3-COOCH$_2$—C$_6$H$_5$ | |
| 739 | " | " | 3-COOCH$_2$-(2,4-Cl$_2$—C$_6$H$_3$) | |
| 740 | " | " | 3-COOCH$_2$CHCH$_2$ | |
| 741 | " | " | 3-COOC$_2$H$_4$CHCH$_2$ | |
| 742 | " | " | 3-COO-n-C$_8$H$_{16}$CHCH$_2$ | |
| 743 | " | " | 3-COO—CH$_2$CCH | |
| 744 | " | " | 3-COO—C$_2$H$_4$—CCH | |
| 745 | " | " | 3-COO-n-C$_5$H$_{10}$CCH | |
| 746 | " | " | 3-COOCH$_2$Si(CH$_3$)$_3$ | |
| 747 | " | " | 3-COOC$_2$H$_4$OCH$_3$ | |
| 748 | " | " | 3-CONH$_2$ | |
| 749 | " | " | 3-CN | |
| 750 | " | " | 3-CONHCH$_3$ | |
| 751 | 4,2-ClCF$_3$ | 5-CH$_3$ | 3-CONHC$_2$H$_5$ | |
| 752 | " | " | 3-CONH-n-C$_3$H$_7$ | |
| 753 | " | " | 3-CONH-n-C$_4$H$_9$ | |
| 754 | " | " | 3-CONH-n-C$_6$H$_{13}$ | |
| 755 | " | " | 3-CONH-n-C$_{10}$H$_{21}$ | |
| 756 | " | " | 3-CONH-i-C$_3$H$_7$ | |
| 757 | " | " | 3-CON(CH$_3$)$_2$ | |
| 758 | " | " | 3-CON(CH$_3$)(nC$_6$H$_{13}$) | |
| 759 | " | " | 3-CON(C$_2$H$_5$)$_2$ | |

TABLE I-continued

Alkyl-aryl-pyrazolecarboxylic acid derivatives

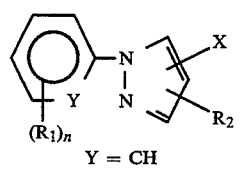

Y = CH (I)

| Example No. | $(R_1)_n$ | $R_2$ | X | Melting point/ boiling point mm Hg [°C.] |
|---|---|---|---|---|
| 760 | " | " | 3-CO—N(piperidinyl) | |
| 761 | " | " | 3-CO—N(pyrrolidinyl) | |
| 762 | " | " | 3-CO—N(morpholinyl) | |
| 763 | " | " | 3-CO—N(2,6-dimethylmorpholinyl) | |
| 764 | " | " | 3-CO—NH-c-$C_6H_{11}$ | |
| 765 | " | " | 3-CO—NH-c-$C_3H_5$ | |
| 766 | " | " | 3-CO—N($CH_3$)(c$C_6H_{11}$) | |
| 767 | " | " | 3-COSH | |
| 768 | " | " | 3-COSNa | |
| 769 | " | " | 3-COS$CH_3$ | |
| 770 | " | " | 3-COS$C_2H_5$ | |
| 771 | " | " | 3-COS$CH_2C_6H_5$ | |
| 772 | " | " | 3-COS-n$C_8H_{17}$ | |
| 773 | " | " | 3-COS$C_2H_4OCH_3$ | |
| 774 | " | " | 3-COS$CH_2CHCH_2$ | |
| 775 | " | " | 3-COS$CH_2CCH$ | |
| 776 | " | " | 3-COS-c-$C_6H_{11}$ | |
| 777 | " | " | 3-COS$CH_2Si(CH_3)_3$ | |
| 778 | " | " | 3-COS-n-$C_4H_8CH(CH_3)_2$ | |
| 779 | " | " | 3-CON(imidazolyl) | |
| 780 | " | " | 3-COO$C_2H_4CH(CH_3)_2$ | |
| 781 | 2,6,4-$Cl_2CF_3$ | 5-$CH_3$ | 3-COO$CH_3$ | |
| 782 | " | " | 3-COO$C_2H_5$ | 138–140 |
| 783 | " | " | 3-COO-n-$C_3H_7$ | |
| 784 | " | " | 3-COO-i-$C_3H_7$ | |
| 785 | " | " | 3-COO-n-$C_4H_9$ | |
| 786 | " | " | 3-COO-n-$C_5H_{11}$ | |
| 787 | " | " | 3-COO-n-$C_6H_{13}$ | |
| 788 | " | " | 3-COO-n-$C_8H_{17}$ | |
| 789 | " | " | 3-COO-n-$C_{10}H_{21}$ | |
| 790 | " | " | 3-C(O)—O—C(O)- pyrazole-aryl anhydride | |
| 791 | " | " | 3-COOH | |
| 792 | " | " | 3-COOLi | |

TABLE I-continued

Alkyl-aryl-pyrazolecarboxylic acid derivatives

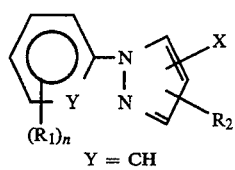

(I)

Y = CH

| Example No. | $(R_1)_n$ | $R_2$ | X | Melting point/ boiling point mm Hg [°C.] |
|---|---|---|---|---|
| 793 | " | " | 3-COONa | |
| 794 | " | " | 3-COOK | |
| 795 | " | " | 3-COOCa$_{1/2}$ | |
| 796 | " | " | 3-COO-c-C$_4$H$_7$ | |
| 797 | " | " | 3-COO-c-C$_6$H$_{11}$ | |
| 798 | " | " | 3-COOCH$_2$—C$_6$H$_5$ | |
| 799 | " | " | 3-COOCH$_2$-(2,4-Cl$_2$—C$_6$H$_3$) | |
| 800 | " | " | 3-COOCH$_2$CHCH$_2$ | |
| 801 | " | " | 3-COOC$_2$H$_4$CHCH$_2$ | |
| 802 | " | " | 3-COO-n-C$_8$H$_{16}$CHCH$_2$ | |
| 803 | " | " | 3-COO—CH$_2$CCH | |
| 804 | " | " | 3-COO—C$_2$H$_4$—CCH | |
| 805 | " | " | 3-COO-n-C$_5$H$_{10}$CCH | |
| 806 | " | " | 3-COOCH$_2$Si(CH$_3$)$_3$ | |
| 807 | " | " | 3-COOC$_2$H$_4$OCH$_3$ | |
| 808 | " | " | 3-CONH$_2$ | |
| 809 | " | " | 3-CN | |
| 810 | " | " | 3-CONHCH$_3$ | |
| 811 | 2,6,4-Cl$_2$CF$_3$ | 5-CH$_3$ | 3-CONHC$_2$H$_5$ | |
| 812 | " | " | 3-CONH-n-C$_3$H$_7$ | |
| 813 | " | " | 3-CONH-n-C$_4$H$_9$ | |
| 814 | " | " | 3-CONH-n-C$_6$H$_{13}$ | |
| 815 | " | " | 3-CONH-n-C$_{10}$H$_{21}$ | |
| 816 | " | " | 3-CONH-i-C$_3$H$_7$ | |
| 817 | " | " | 3-CON(CH$_3$)$_2$ | |
| 818 | " | " | 3-CON(CH$_3$)(nC$_6$H$_{13}$) | |
| 819 | " | " | 3-CON(C$_2$H$_5$)$_2$ | |
| 820 | " | " | 3-CO—N(piperidinyl) | |
| 821 | " | " | 3-CO—N(pyrrolidinyl) | |
| 822 | " | " | 3-CO—N(morpholinyl) | |
| 823 | " | " | 3-CO—N(2,6-dimethylmorpholinyl) | |
| 824 | " | " | 3-CO—NH-c-C$_6$H$_{11}$ | |
| 825 | " | " | 3-CO—NH-c-C$_3$H$_5$ | |
| 826 | " | " | 3-CO—N(CH$_3$)(cC$_6$H$_{11}$) | |
| 827 | " | " | 3-COSH | |
| 828 | " | " | 3-COSNa | |
| 829 | " | " | 3-COSCH$_3$ | |
| 830 | " | " | 3-COSC$_2$H$_5$ | |
| 831 | " | " | 3-COSCH$_2$C$_6$H$_5$ | |
| 832 | " | " | 3-COS-nC$_8$H$_{17}$ | |
| 833 | " | " | 3-COSC$_2$H$_4$OCH$_3$ | |
| 834 | " | " | 3-COSCH$_2$CHCH$_2$ | |
| 835 | " | " | 3-COSCH$_2$CCH | |
| 836 | " | " | 3-COS-c-C$_6$H$_{11}$ | |
| 837 | " | " | 3-COSCH$_2$Si(CH$_3$)$_3$ | |
| 838 | " | " | 3-COS-n-C$_4$H$_8$CH(CH$_3$)$_2$ | |

TABLE I-continued

Alkyl-aryl-pyrazolecarboxylic acid derivatives

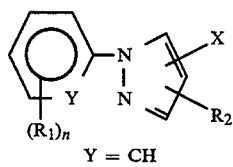

Y = CH

| Example No. | $(R_1)_n$ | $R_2$ | X | Melting point/ boiling point mm Hg [°C.] |
|---|---|---|---|---|
| 839 | " | " | 3-CON⟨pyrazolyl⟩ | |
| 840 | " | " | 3-COOC$_2$H$_4$CH(CH$_3$)$_2$ | |
| 841 | 3,5-Cl—CF$_3$ | 5-CH$_3$ | 3-COOCH$_3$ | |
| 842 | " | " | 3-COOC$_2$H$_5$ | 55–58 |
| 843 | " | " | 3-COO-n-C$_3$H$_7$ | |
| 844 | " | " | 3-COO-i-C$_3$H$_7$ | |
| 845 | " | " | 3-COO-n-C$_4$H$_9$ | |
| 846 | " | " | 3-COO-n-C$_5$H$_{11}$ | |
| 847 | " | " | 3-COO-n-C$_6$H$_{13}$ | |
| 848 | " | " | 3-COO-n-C$_8$H$_{17}$ | |
| 849 | " | " | 3-COO-n-C$_{10}$H$_{21}$ | |
| 850 | " | " | 3-C(O)-O-C(O)- pyrazole-aryl structure | |
| 851 | " | " | 3-COOH | |
| 852 | " | " | 3-COOLi | |
| 853 | " | " | 3-COONa | |
| 854 | " | " | 3-COOK | |
| 855 | " | " | 3-COOCa$_{1/2}$ | |
| 856 | " | " | 3-COO-c-C$_4$H$_7$ | |
| 857 | " | " | 3-COO-c-C$_6$H$_{11}$ | |
| 858 | " | " | 3-COOCH$_2$—C$_6$H$_5$ | |
| 859 | " | " | 3-COOCH$_2$-(2,4-Cl$_2$—C$_6$H$_3$) | |
| 860 | " | " | 3-COOCH$_2$CHCH$_2$ | |
| 861 | " | " | 3-COOC$_2$H$_4$CHCH$_2$ | |
| 862 | " | " | 3-COO-n-C$_8$H$_{16}$CHCH$_2$ | |
| 863 | " | " | 3-COO—CH$_2$CCH | |
| 864 | " | " | 3-COO—C$_2$H$_4$—CCH | |
| 865 | " | " | 3-COO-n-C$_5$H$_{10}$CCH | |
| 866 | " | " | 3-COOCH$_2$Si(CH$_3$)$_3$ | |
| 867 | " | " | 3-COOC$_2$H$_4$OCH$_3$ | |
| 868 | " | " | 3-CONH$_2$ | |
| 869 | " | " | 3-CN | |
| 870 | " | " | 3-CONHCH$_3$ | |
| 871 | 3,5-ClCF$_3$ | 5-CH$_3$ | 3-CONHC$_2$H$_5$ | |
| 872 | " | " | 3-CONH-n-C$_3$H$_7$ | |
| 873 | " | " | 3-CONH-n-C$_4$H$_9$ | |
| 874 | " | " | 3-CONH-n-C$_6$H$_{13}$ | |
| 875 | " | " | 3-CONH-n-C$_{10}$H$_{21}$ | |
| 876 | " | " | 3-CONH-i-C$_3$H$_7$ | |
| 877 | " | " | 3-CON(CH$_3$)$_2$ | |
| 878 | " | " | 3-CON(CH$_3$)(nC$_6$H$_{13}$) | |
| 879 | " | " | 3-CON(C$_2$H$_5$)$_2$ | |
| 880 | " | " | 3-CO—N(piperidinyl) | |
| 881 | " | " | 3-CO—N(pyrrolidinyl) | |

TABLE I-continued

Alkyl-aryl-pyrazolecarboxylic acid derivatives

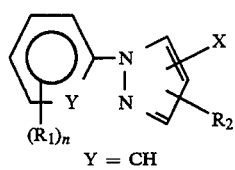

Y = CH (I)

| Example No. | $(R_1)_n$ | $R_2$ | X | Melting point/ boiling point mm Hg [°C.] |
|---|---|---|---|---|
| 882 | " | " | 3-CO—N(morpholino) | |
| 883 | " | " | 3-CO—N(2,6-dimethylmorpholino) | |
| 884 | " | " | 3-CO—NH-c-$C_6H_{11}$ | |
| 885 | " | " | 3-CO—NH-c-$C_3H_5$ | |
| 886 | " | " | 3-CO—N($CH_3$)(c$C_6H_{11}$) | |
| 887 | " | " | 3-COSH | |
| 888 | " | " | 3-COSNa | |
| 889 | " | " | 3-COS$CH_3$ | |
| 890 | " | " | 3-COS$C_2H_5$ | |
| 891 | " | " | 3-COS$CH_2C_6H_5$ | |
| 892 | " | " | 3-COS-n-$C_8H_{17}$ | |
| 893 | " | " | 3-COS$C_2H_4OCH_3$ | |
| 894 | " | " | 3-COS$CH_2CHCH_2$ | |
| 895 | " | " | 3-COS$CH_2CCH$ | |
| 896 | " | " | 3-COS-c-$C_6H_{11}$ | |
| 897 | " | " | 3-COS$CH_2Si(CH_3)_3$ | |
| 898 | " | " | 3-COS-n-$C_4H_8CH(CH_3)_2$ | |
| 899 | " | " | 3-CON(imidazol-1-yl) | |
| 900 | " | " | 3-COO$C_2H_4CH(CH_3)_2$ | |
| 901 | 3,5-Cl$CF_3$ | 3-$CH_3$ | 5-COO$CH_3$ | |
| 902 | " | " | 5-COO$C_2H_5$ | Oil |
| 903 | " | " | 5-COO-n-$C_3H_7$ | |
| 904 | " | " | 5-COO-i-$C_3H_7$ | |
| 905 | " | " | 5-COO-n-$C_4H_9$ | |
| 906 | " | " | 5-COO-n-$C_5H_{11}$ | |
| 907 | " | " | 5-COO-n-$C_6H_{13}$ | |
| 908 | " | " | 5-COO-n-$C_8H_{17}$ | |
| 909 | " | " | 5-COO-n-$C_{10}H_{21}$ | |
| 910 | " | " | (anhydride structure) | |
| 911 | " | " | 5-COOH | |
| 912 | " | " | 5-COOLi | |
| 913 | " | " | 5-COONa | |
| 914 | " | " | 5-COOK | |
| 915 | " | " | 5-COOCa$_{1/2}$ | |
| 916 | " | " | 5-COO-c-$C_4H_7$ | |
| 917 | " | " | 5-COO-c-$C_6H_{11}$ | |
| 918 | " | " | 5-COO$CH_2$—$C_6H_5$ | |
| 919 | " | " | 5-COO$CH_2$-(2,4-$Cl_2$—$C_6H_3$) | |
| 920 | " | " | 5-COO$CH_2CHCH_2$ | |
| 921 | " | " | 5-COO$C_2H_4CHCH_2$ | |
| 922 | " | " | 5-COO-n-$C_8H_{16}CHCH_2$ | |
| 923 | " | " | 5-COO—$CH_2CCH$ | |
| 924 | " | " | 5-COO—$C_2H_4$—CCH | |

TABLE I-continued
Alkyl-aryl-pyrazolecarboxylic acid derivatives

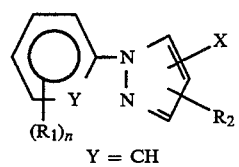

Y = CH

| Example No. | (R₁)ₙ | R₂ | X | Melting point/ boiling point mm Hg [°C.] |
|---|---|---|---|---|
| 925 | " | " | 5-COO-n-C₅H₁₀CCH | |
| 926 | " | " | 5-COOCH₂Si(CH₃)₃ | |
| 927 | " | " | 5-COOC₂H₄OCH₃ | |
| 928 | " | " | 5-CONH₂ | |
| 929 | " | " | 5-CN | |
| 930 | " | " | 5-CONHCH₃ | |
| 931 | 3,5-Cl—CF₃ | 3-CH₃ | 5-CONHC₂H₅ | |
| 932 | " | " | 5-CONH-n-C₃H₇ | |
| 933 | " | " | 5-CONH-n-C₄H₉ | |
| 934 | " | " | 5-CONH-n-C₆H₁₃ | |
| 935 | " | " | 5-CONH-n-C₁₀H₂₁ | |
| 936 | " | " | 5-CONH-i-C₃H₇ | |
| 937 | " | " | 5-CON(CH₃)₂ | |
| 938 | " | " | 5-CON(CH₃)(nC₆H₁₃) | |
| 939 | " | " | 5-CON(C₂H₅)₂ | |
| 940 | " | " | 5-CO—N(piperidinyl) | |
| 941 | " | " | 5-CO—N(pyrrolidinyl) | |
| 942 | " | " | 5-CO—N(morpholinyl) | |
| 943 | " | " | 5-CO—N(2,6-dimethylmorpholinyl) | |
| 944 | " | " | 5-CO—NH-c-C₆H₁₁ | |
| 945 | " | " | 5-CO—NH-c-C₃H₅ | |
| 946 | " | " | 5-CO—N(CH₃)(cC₆H₁₁) | |
| 947 | " | " | 5-COSH | |
| 948 | " | " | 5-COSNa | |
| 949 | " | " | 5-COSCH₃ | |
| 950 | " | " | 5-COSC₂H₅ | |
| 951 | " | " | 5-COSCH₂C₆H₅ | |
| 952 | " | " | 5-COS-nC₈H₁₇ | |
| 953 | " | " | 5-COSC₂H₄OCH₃ | |
| 954 | " | " | 5-COSCH₂CHCH₂ | |
| 955 | " | " | 5-COSCH₂CCH | |
| 956 | " | " | 5-COS-c-C₆H₁₁ | |
| 957 | " | " | 5-COSCH₂Si(CH₃)₃ | |
| 958 | " | " | 5-COS-n-C₄H₈CH(CH₃)₂ | |
| 959 | " | " | 5-CON(imidazolyl) | |
| 960 | " | " | 5-COOC₂H₄CH(CH₃)₂ | |
| 961 | 2,3-Cl₂ | 5-CH₃ | 3-COOCH₃ | |
| 962 | " | " | 3-COOC₂H₅ | 77–79 |
| 963 | " | " | 3-COO-n-C₃H₇ | |

TABLE I-continued

Alkyl-aryl-pyrazolecarboxylic acid derivatives

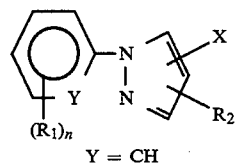

Y = CH (I)

| Example No. | $(R_1)_n$ | $R_2$ | X | Melting point/ boiling point mm Hg [°C.] |
|---|---|---|---|---|
| 964 | " | " | 3-COO-i-$C_3H_7$ | |
| 965 | " | " | 3-COO-n-$C_4H_9$ | |
| 966 | " | " | 3-COO-n-$C_5H_{11}$ | |
| 967 | " | " | 3-COO-n-$C_6H_{13}$ | |
| 968 | " | " | 3-COO-n-$C_8H_{17}$ | |
| 969 | " | " | 3-COO-n-$C_{10}H_{21}$ | |
| 970 | " | " | ![anhydride structure: 3-C(=O)-O-C(=O)- linked to pyrazole with $R_2$ and N-N-aryl-$(R_1)_n$, Y] | |
| 971 | " | " | 3-COOH | |
| 972 | " | " | 3-COOLi | |
| 973 | " | " | 3-COONa | |
| 974 | " | " | 3-COOK | |
| 975 | " | " | 3-COOCa$_{1/2}$ | |
| 976 | " | " | 3-COO-c-$C_4H_7$ | |
| 977 | " | " | 3-COO-c-$C_6H_{11}$ | |
| 978 | " | " | 3-COOCH$_2$—$C_6H_5$ | |
| 979 | " | " | 3-COOCH$_2$-(2,4-Cl$_2$—$C_6H_3$) | |
| 980 | " | " | 3-COOCH$_2$CHCH$_2$ | |
| 981 | " | " | 3-COOC$_2$H$_4$CHCH$_2$ | |
| 982 | " | " | 3-COO-n-C$_8$H$_{16}$CHCH$_2$ | |
| 983 | " | " | 3-COO—CH$_2$CCH | |
| 984 | " | " | 3-COO—C$_2$H$_4$—CCH | |
| 985 | " | " | 3-COO-n-C$_5$H$_{10}$CCH | |
| 986 | " | " | 3-COOCH$_2$Si(CH$_3$)$_3$ | |
| 987 | " | " | 3-COOC$_2$H$_4$OCH$_3$ | |
| 988 | " | " | 3-CONH$_2$ | |
| 989 | " | " | 3-CN | |
| 990 | " | " | 3-CONHCH$_3$ | |
| 991 | 2,3-Cl$_2$ | 5-CH$_3$ | 3-CONHC$_2$H$_5$ | |
| 992 | " | " | 3-CONH-n-C$_3$H$_7$ | |
| 993 | " | " | 3-CONH-n-C$_4$H$_9$ | |
| 994 | " | " | 3-CONH-n-C$_6$H$_{13}$ | |
| 995 | " | " | 3-CONH-n-C$_{10}$H$_{21}$ | |
| 996 | " | " | 3-CONH-i-C$_3$H$_7$ | |
| 997 | " | " | 3-CON(CH$_3$)$_2$ | |
| 998 | " | " | 3-CON(CH$_3$)(nC$_6$H$_{13}$) | |
| 999 | " | " | 3-CON(C$_2$H$_5$)$_2$ | |
| 1000 | " | " | 3-CO—N(piperidinyl) | |
| 1001 | " | " | 3-CO—N(pyrrolidinyl) | |
| 1002 | " | " | 3-CO—N(morpholinyl) | |

TABLE I-continued

Alkyl-aryl-pyrazolecarboxylic acid derivatives

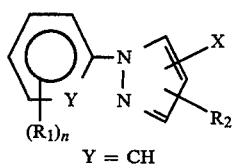

Y = CH

| Example No. | (R$_1$)$_n$ | R$_2$ | X | Melting point/ boiling point mm Hg [°C.] |
|---|---|---|---|---|
| 1003 | " | " | 3-CO—N⟨morpholino⟩ | |
| 1004 | " | " | 3-CO—NH-c-C$_6$H$_{11}$ | |
| 1005 | " | " | 3-CO—NH-c-C$_3$H$_5$ | |
| 1006 | " | " | 3-CO—N(CH$_3$)(cC$_6$H$_{11}$) | |
| 1007 | " | " | 3-COSH | |
| 1008 | " | " | 3-COSNa | |
| 1009 | " | " | 3-COSCH$_3$ | |
| 1010 | " | " | 3-COSC$_2$H$_5$ | |
| 1011 | " | " | 3-COSCH$_2$C$_6$H$_5$ | |
| 1012 | " | " | 3-COS-nC$_8$H$_{17}$ | |
| 1013 | " | " | 3-COSC$_2$H$_4$OCH$_3$ | |
| 1014 | " | " | 3-COSCH$_2$CHCH$_2$ | |
| 1015 | " | " | 3-COSCH$_2$CCH | |
| 1016 | " | " | 3-COS-c-C$_6$H$_{11}$ | |
| 1017 | " | " | 3-COSCH$_2$Si(CH$_3$)$_3$ | |
| 1018 | " | " | 3-COS-n-C$_4$H$_8$CH(CH$_3$)$_2$ | |
| 1019 | " | " | 3-CON⟨imidazolyl⟩ | |
| 1020 | " | " | 3-COOC$_2$H$_4$CH(CH$_3$)$_2$ | |
| 1021 | 2,4,5-Cl$_2$OCH$_3$ | 5-CH$_3$ | 3-COOCH$_3$ | |
| 1022 | " | " | 3-COOC$_2$H$_5$ | 155–159 |
| 1023 | " | " | 3-COO-n-C$_3$H$_7$ | |
| 1024 | " | " | 3-COO-i-C$_3$H$_7$ | |
| 1025 | " | " | 3-COO-n-C$_4$H$_9$ | |
| 1026 | " | " | 3-COO-n-C$_5$H$_{11}$ | |
| 1027 | " | " | 3-COO-n-C$_6$H$_{13}$ | |
| 1028 | " | " | 3-COO-n-C$_8$H$_{17}$ | |
| 1029 | " | " | 3-COO-n-C$_{10}$H$_{21}$ | |
| 1030 | " | " | 3-C(O)-O-C(O)- anhydride dimer | |
| 1031 | " | " | 3-COOH | |
| 1032 | " | " | 3-COOLi | |
| 1033 | " | " | 3-COONa | |
| 1034 | " | " | 3-COOK | |
| 1035 | " | " | 3-COOCa$_{1/2}$ | |
| 1036 | " | " | 3-COO-c-C$_4$H$_7$ | |
| 1037 | " | " | 3-COO-c-C$_6$H$_{11}$ | |
| 1038 | " | " | 3-COOCH$_2$—C$_6$H$_5$ | |
| 1039 | " | " | 3-COOCH$_2$-(2,4-Cl$_2$—C$_6$H$_3$) | |
| 1040 | " | " | 3-COOCH$_2$CHCH$_2$ | |
| 1041 | " | " | 3-COOC$_2$H$_4$CHCH$_2$ | |
| 1042 | " | " | 3-COO-n-C$_8$H$_{16}$CHCH$_2$ | |
| 1043 | " | " | 3-COO—CH$_2$CCH | |
| 1044 | " | " | 3-COO—C$_2$H$_4$—CCH | |
| 1045 | " | " | 3-COO-n-C$_5$H$_{10}$CCH | |
| 1046 | " | " | 3-COOCH$_2$Si(CH$_3$)$_3$ | |
| 1047 | " | " | 3-COOC$_2$H$_4$OCH$_3$ | |
| 1048 | " | " | 3-CONH$_2$ | |
| 1049 | " | " | 3-CN | |
| 1050 | " | " | 3-CONHCH$_3$ | |

TABLE I-continued

Alkyl-aryl-pyrazolecarboxylic acid derivatives

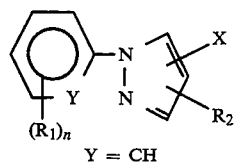

Y = CH

| Example No. | (R₁)ₙ | R₂ | X | Melting point/ boiling point mm Hg [°C.] |
|---|---|---|---|---|
| 1051 | 2,4,5-Cl₂OCH₃ | 5-CH₃ | 3-CONHC₂H₅ | |
| 1052 | " | " | 3-CONH-n-C₃H₇ | |
| 1053 | " | " | 3-CONH-n-C₄H₉ | |
| 1054 | " | " | 3-CONH-n-C₆H₁₃ | |
| 1055 | " | " | 3-CONH-n-C₁₀H₂₁ | |
| 1056 | " | " | 3-CONH-i-C₃H₇ | |
| 1057 | " | " | 3-CON(CH₃)₂ | |
| 1058 | " | " | 3-CON(CH₃)(nC₆H₁₃) | |
| 1059 | " | " | 3-CON(C₂H₅)₂ | |
| 1060 | " | " | 3-CO—N(piperidine) | |
| 1061 | " | " | 3-CO—N(pyrrolidine) | |
| 1062 | " | " | 3-CO—N(morpholine) | |
| 1063 | " | " | 3-CO—N(2,6-dimethylmorpholine) | |
| 1064 | " | " | 3-CO—NH-c-C₆H₁₁ | |
| 1065 | " | " | 3-CO—NH-c-C₃H₅ | |
| 1066 | " | " | 3-CO—N(CH₃)(cC₆H₁₁) | |
| 1067 | " | " | 3-COSH | |
| 1068 | " | " | 3-COSNa | |
| 1069 | " | " | 3-COSCH₃ | |
| 1070 | " | " | 3-COSC₂H₅ | |
| 1071 | " | " | 3-COSCH₂C₆H₅ | |
| 1072 | " | " | 3-COS-nC₈H₁₇ | |
| 1073 | " | " | 3-COSC₂H₄OCH₃ | |
| 1074 | " | " | 3-COSCH₂CHCH₂ | |
| 1075 | " | " | 3-COSCH₂CCH | |
| 1076 | " | " | 3-COS-c-C₆H₁₁ | |
| 1077 | " | " | 3-COSCH₂Si(CH₃)₃ | |
| 1078 | " | " | 3-COS-n-C₄H₈CH(CH₃)₂ | |
| 1079 | " | " | 3-CON(imidazole) | |
| 1080 | " | " | 3-COOC₂H₄CH(CH₃)₂ | |
| 1081 | 2,4,5-Cl₂OCH₃ | 3-CH₃ | 5-COOCH₃ | |
| 1082 | " | " | 5-COOC₂H₅ | Oil |
| 1083 | " | " | 5-COO-n-C₃H₇ | |
| 1084 | " | " | 5-COO-i-C₃H₇ | |
| 1085 | " | " | 5-COO-n-C₄H₉ | |
| 1086 | " | " | 5-COO-n-C₅H₁₁ | |
| 1087 | " | " | 5-COO-n-C₆H₁₃ | |
| 1088 | " | " | 5-COO-n-C₈H₁₇ | |
| 1089 | " | " | 5-COO-n-C₁₀H₂₁ | |

TABLE I-continued

Alkyl-aryl-pyrazolecarboxylic acid derivatives

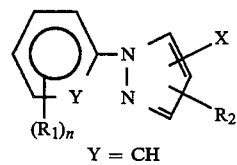

Y = CH

| Example No. | (R₁)ₙ | R₂ | X | Melting point/ boiling point mm Hg [°C.] |
|---|---|---|---|---|
| 1090 | " | " | 5-C(=O)-O-C(=O) pyrazole-N-N-aryl(R₁)ₙ with R₂, Y | |
| 1091 | " | " | 5-COOH | |
| 1092 | " | " | 5-COOLi | |
| 1093 | " | " | 5-COONa | |
| 1094 | " | " | 5-COOK | |
| 1095 | " | " | 5-COOCa₁/₂ | |
| 1096 | " | " | 5-COO-c-C₄H₇ | |
| 1097 | " | " | 5-COO-c-C₆H₁₁ | |
| 1098 | " | " | 5-COOCH₂—C₆H₅ | |
| 1099 | " | " | 5-COOCH₂-(2,4-Cl₂—C₆H₃) | |
| 1100 | " | " | 5-COOCH₂CHCH₂ | |
| 1101 | " | " | 5-COOC₂H₄CHCH₂ | |
| 1102 | " | " | 5-COO-n-C₈H₁₆CHCH₂ | |
| 1103 | " | " | 5-COO—CH₂CCH | |
| 1104 | " | " | 5-COO—C₂H₄—CCH | |
| 1105 | " | " | 5-COO-n-C₅H₁₀CCH | |
| 1106 | " | " | 5-COOCH₂Si(CH₃)₃ | |
| 1107 | " | " | 5-COOC₂H₄OCH₃ | |
| 1108 | " | " | 5-CONH₂ | |
| 1109 | " | " | 5-CN | |
| 1110 | " | " | 5-CONHCH₃ | |
| 1111 | 2,4,5-Cl₂OCH₃ | 3-CH₃ | 5-CONHC₂H₅ | |
| 1112 | " | " | 5-CONH-n-C₃H₇ | |
| 1113 | " | " | 5-CONH-n-C₄H₉ | |
| 1114 | " | " | 5-CONH-n-C₆H₁₃ | |
| 1115 | " | " | 5-CONH-n-C₁₀H₂₁ | |
| 1116 | " | " | 5-CONH-i-C₃H₇ | |
| 1117 | " | " | 5-CON(CH₃)₂ | |
| 1118 | " | " | 5-CON(CH₃)(nC₆H₁₃) | |
| 1119 | " | " | 5-CON(C₂H₅)₂ | |
| 1120 | " | " | 5-CO—N(piperidine) | |
| 1121 | " | " | 5-CO—N(pyrrolidine) | |
| 1122 | " | " | 5-CO—N(morpholine) | |
| 1123 | " | " | 5-CO—N(2,6-dimethylmorpholine) | |
| 1124 | " | " | 5-CO—NH-c-C₆H₁₁ | |
| 1125 | " | " | 5-CO—NH-c-C₃H₅ | |
| 1126 | " | " | 5-CO—N(CH₃)(cC₆H₁₁) | |
| 1127 | " | " | 5-COSH | |

TABLE I-continued

Alkyl-aryl-pyrazolecarboxylic acid derivatives

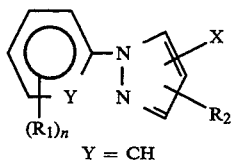

Y = CH (I)

| Example No. | (R$_1$)$_n$ | R$_2$ | X | Melting point/ boiling point mm Hg [°C.] |
|---|---|---|---|---|
| 1128 | " | " | 5-COSNa | |
| 1129 | " | " | 5-COSCH$_3$ | |
| 1130 | " | " | 5-COSC$_2$H$_5$ | |
| 1131 | " | " | 5-COSCH$_2$C$_6$H$_5$ | |
| 1132 | " | " | 5-COS-nC$_8$H$_{17}$ | |
| 1133 | " | " | 5-COSC$_2$H$_4$OCH$_3$ | |
| 1134 | " | " | 5-COSCH$_2$CHCH$_2$ | |
| 1135 | " | " | 5-COSCH$_2$CCH | |
| 1136 | " | " | 5-COS-c-C$_6$H$_{11}$ | |
| 1137 | " | " | 5-COSCH$_2$Si(CH$_3$)$_3$ | |
| 1138 | " | " | 5-COS-n-C$_4$H$_8$CH(CH$_3$)$_2$ | |
| 1139 | " | " | 5-CON⟨imidazole⟩ | |
| 1140 | " | " | 5-COOC$_2$H$_4$CH(CH$_3$)$_2$ | |
| 1141 | 2,6,3-(C$_2$H$_5$)$_2$Cl | 5-CH$_3$ | 3-COOCH$_3$ | |
| 1142 | " | " | 3-COOC$_2$H$_5$ | Oil |
| 1143 | " | " | 3-COO-n-C$_3$H$_7$ | |
| 1144 | " | " | 3-COO-i-C$_3$H$_7$ | |
| 1145 | " | " | 3-COO-n-C$_4$H$_9$ | |
| 1146 | " | " | 3-COO-n-C$_5$H$_{11}$ | |
| 1147 | " | " | 3-COO-n-C$_6$H$_{13}$ | |
| 1148 | " | " | 3-COO-n-C$_8$H$_{17}$ | |
| 1149 | " | " | 3-COO-n-C$_{10}$H$_{21}$ | |
| 1150 | " | " | 3-C(O)-O-C(O)-[pyrazole-aryl] | |
| 1151 | " | " | 3-COOH | |
| 1152 | " | " | 3-COOLi | |
| 1153 | " | " | 3-COONa | |
| 1154 | " | " | 3-COOK | |
| 1155 | " | " | 3-COOCa$_{1/2}$ | |
| 1156 | " | " | 3-COO-c-C$_4$H$_7$ | |
| 1157 | " | " | 3-COO-c-C$_6$H$_{11}$ | |
| 1158 | " | " | 3-COOCH$_2$—C$_6$H$_5$ | |
| 1159 | " | " | 3-COOCH$_2$-(2,4-Cl$_2$—C$_6$H$_3$) | |
| 1160 | " | " | 3-COOCH$_2$CHCH$_2$ | |
| 1161 | " | " | 3-COOC$_2$H$_4$CHCH$_2$ | |
| 1162 | " | " | 3-COO-n-C$_8$H$_{16}$CHCH$_3$ | |
| 1163 | " | " | 3-COO—CH$_2$CCH | |
| 1164 | " | " | 3-COO—C$_2$H$_4$—CCH | |
| 1165 | " | " | 3-COO-n-C$_5$H$_{10}$CCH | |
| 1166 | " | " | 3-COOCH$_2$Si(CH$_3$)$_3$ | |
| 1167 | " | " | 3-COOC$_2$H$_4$OCH$_3$ | |
| 1168 | " | " | 3-CONH$_2$ | |
| 1169 | " | " | 3-CN | |
| 1170 | " | " | 3-CONHCH$_3$ | |
| 1171 | 2,6,3-(C$_2$H$_5$)$_2$Cl | 5-CH$_3$ | 3-CONHC$_2$H$_5$ | |
| 1172 | " | " | 3-CONH-n-C$_3$H$_7$ | |
| 1173 | " | " | 3-CONH-n-C$_4$H$_9$ | |
| 1174 | " | " | 3-CONH-n-C$_6$H$_{13}$ | |
| 1175 | " | " | 3-CONH-n-C$_{10}$H$_{21}$ | |
| 1176 | " | " | 3-CONH-i-C$_3$H$_7$ | |
| 1177 | " | " | 3-CON(CH$_3$)$_2$ | |
| 1178 | " | " | 3-CON(CH$_3$)(nC$_6$H$_{13}$) | |
| 1179 | " | " | 3-CON(C$_2$H$_5$)$_2$ | |

TABLE I-continued

Alkyl-aryl-pyrazolecarboxylic acid derivatives

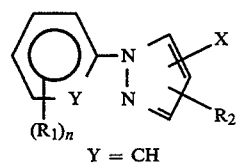

Y = CH

| Example No. | $(R_1)_n$ | $R_2$ | X | Melting point/ boiling point mm Hg [°C.] |
|---|---|---|---|---|
| 1180 | " | " | 3-CO—N⟨piperidine⟩ | |
| 1181 | " | " | 3-CO—N⟨pyrrolidine⟩ | |
| 1182 | " | " | 3-CO—N⟨morpholine⟩ | |
| 1183 | " | " | 3-CO—N⟨dimethylmorpholine⟩ | |
| 1184 | " | " | 3-CO—NH-c-$C_6H_{11}$ | |
| 1185 | " | " | 3-CO—NH-c-$C_3H_5$ | |
| 1186 | " | " | 3-CO—N($CH_3$)(c$C_6H_{11}$) | |
| 1187 | " | " | 3-COSH | |
| 1188 | " | " | 3-COSNa | |
| 1189 | " | " | 3-COS$CH_3$ | |
| 1190 | " | " | 3-COS$C_2H_5$ | |
| 1191 | " | " | 3-COS$CH_2C_6H_5$ | |
| 1192 | " | " | 3-COS-n$C_8H_{17}$ | |
| 1193 | " | " | 3-COS$C_2H_4OCH_3$ | |
| 1194 | " | " | 3-COS$CH_2CHCH_2$ | |
| 1195 | " | " | 3-COS$CH_2CCH$ | |
| 1196 | " | " | 3-COS-c-$C_6H_{11}$ | |
| 1197 | " | " | 3-COS$CH_2Si(CH_3)_3$ | |
| 1198 | " | " | 3-COS-n-$C_4H_8CH(CH_3)_2$ | |
| 1199 | " | " | 3-CON⟨imidazole⟩ | |
| 1200 | " | " | 3-COO$C_2H_4CH(CH_3)_2$ | |
| 1201 | 3-$CF_3$ | 3-$CH_3$ | 5-COOH | 164–170 |
| 1202 | 3,2,6-Cl($C_2H_5)_2$ | " | 5-COO$C_2H_5$ | Oil |
| 1203 | 4,2-Cl—$CF_3$—Phe | 3-$CH_6$ | 5-COO$C_2H_5$ | Oil |
| 1204 | 3-$CF_3$ | 5-C($CH_3)_3$ | 3-COO$C_2H_5$ | Oil |
| 1205 | 2,4-$Br_2$ | 5-C($CH_3)_3$ | 3-COO$C_2H_5$ | 130–132 |
| 1206 | 2,3-$Cl_2$ | 5-C($CH_3)_3$ | 3-COO$C_2H_5$ | 101–102 |
| 1207 | 2,6,4-$Cl_2$—$CF_3$ | 3-$CH_2CH(CH_3)_2$ | 5-COO$C_2H_5$ | Oil |
| 1208 | " | 5-$CH_2CH(CH_3)_2$ | 3-COO$C_2H_5$ | 82–84 |
| 1209 | 2,4-$Cl_2$ | 3-$CH_2CH(CH_3)_2$ | 5-COO$C_2H_5$ | Oil |
| 1210 | 2,4-$Br_2$ | 3-i-$C_3H_7$ | 5-COO$C_2H_5$ | |
| 1211 | 3-$CF_3$ | 5-$CH_2CH(CH_3)_2$ | 3-COO$C_2H_5$ | Oil |
| 1212 | 2,6,4-$Cl_2$—$CF_3$ | 5-$CH_2CH(CH_3)_2$ | 3-COOH | 191–193 |
| 1213 | 2,3-$Cl_2$—Phe | 5-CH | 3-COO$C_2H_5$ | 76–78 |
| 1214 | " | 5-$CH_2CH(CH_3)$ | 3-COO$C_2H_5$ | 91–92 |
| 1215 | 2,4-$Br_2$ | 5-$CH_2CH(CH_3)$ | 3-COOEt | Oil |
| 1216 | 2,4-$Cl_2$ | 5-$CH_3$ | 3-COO$CH_2CH(CH_3)CH_2CH_3$ | 39–45 |
| 1217 | 3-$CF_3$ | 5-$CH_3$ | 3-COO$C_2H_5$ | Oil |
| 1218 | 2,4-$Br_2$ | 5-$CH(CH_3)_2$ | 3-COO$C_2H_5$ | 72–79 |
| 1219 | 2,4-Cl—$CF_3$ | 3-$CH(CH_3)_2$ | 5-COO$C_2H_5$ | Oil |

TABLE I-continued

Alkyl-aryl-pyrazolecarboxylic acid derivatives

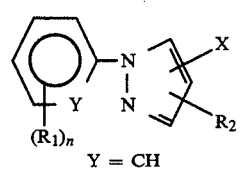

Y = CH (I)

| Example No. | $(R_1)_n$ | $R_2$ | X | Melting point/ boiling point mm Hg [°C.] |
| --- | --- | --- | --- | --- |
| 1220 | " | 5-CH(CH$_3$)$_2$ | 3-COOC$_2$H$_5$ | 58–70 |
| 1221 | 2,4-Br$_2$ | 5-CH$_2$CH(CH$_3$)$_2$ | 3-COOC$_2$H$_5$ | 184–187 |
| 1222 | 2,4-Cl—CF$_3$ | 5-C(CH$_3$)$_3$ | 3-COOC$_2$H$_5$ | 106–107 |
| 1223 | 2,6,4-Cl$_2$—CF$_3$ | 5-CH$_2$CH(CH$_3$)$_2$ | 3-COO$^-$Li$^+$ | >250 |
| 1224 | 2,3-Cl$_2$ | 5-CH$_2$CH(CH$_3$)$_2$ | 3-COOH | 209–211 |
| 1225 | 2,4-Cl—CF$_3$ | 5-CH$_2$CH(CH$_3$)$_2$ | 3-COOC$_2$H$_5$ | 54–58 |
| 1226 | 2,4,5-Cl, F—CH$_3$—Phe | 5-CH$_3$ | 3-COOC$_2$H$_5$ | 109–110 |
| 1227 | 3,4-Cl, —CH$_3$—Phe | 5-CH$_3$ | 3-COOC$_2$H$_5$ | 77–80 |
| 1228 | 2,4-Cl$_2$—Phe | 5-CH$_3$ | 3-COO HN(C$_2$H$_4$OH)$_3$ | 135–138 |
| 1229 | 2,4-Cl$_2$—Phe | 5-CH$_3$ | 3-CONHC(CH$_3$)(CH(CH$_3$)$_2$)—CONH$_2$ | 65–69 |
| 1230 | 2,4-Cl$_2$—Phe | 5-CH$_3$ | 3-C(NH$_2$)NOH | 205 |
| 1231 | 2,6-(CH$_3$)$_2$ | 5-CH$_3$ | 3-COOC$_2$H$_5$ | Oil |
| 1232 | 4-F—Phe | 5-CH$_3$ | 3-COOC$_2$H$_5$ | Resin |
| 1233 | 4-OCH$_3$—Phe | 5-CH$_3$ | 3-COOC$_2$H$_5$ | Oil |
| 1234 | 2,4-Cl, CF$_3$—Phe | 3-CH$_3$ | 5-COOC$_2$H$_5$ | Oil |
| 1235 | 2,4-Cl$_2$ | 5-c-C$_3$H$_5$ | 3-COOC$_2$H$_5$ | 80 |
| 1236 | 2,6,4-Cl$_2$, CF$_3$—Phe | 5-c-C$_3$H$_5$ | 3-COOC$_2$H$_5$ | 105–110 |

Abbreviations:
n: straight-chain
i: iso (branched)
c: cyclo

C. Biological Examples

Example 1

Wheat and barley were grown to the 3- to 4-leaf stage in plastic pots in a greenhouse and were then treated in succession by the post-emergence method with the safener compounds and the herbicides tested. The herbicides and the compounds of the formula I were applied here in the form of aqueous suspensions or emulsions with a water application amount, when converted, of 800 l/ha. 3 to 4 weeks after the treatment, the plants were rated visually for any type of damage by the herbicides applied, the extent of the persistent inhibition of growth being taken into particular account. The degree of damage or the safener action of I was determined in % damage.

The results from Table I illustrate that the compounds according to the invention can effectively reduce severe herbicide damage to the crop plants.

Even in cases of high overdoses of the herbicide, severe damage occurring to the crop plants is significantly reduced, and milder damage is eliminated completely. Mixtures of herbicides and compounds according to the invention are therefore advantageously suitable for selectively combating weeds in cereal crops.

TABLE 1

Safener action of the compounds according to the invention

| Combination Herbicide/Safener | Dosage (kg of a.s./ha) | % damage (safener action) | |
| --- | --- | --- | --- |
| | | TA | HV |
| H1 | 2.0 | 80 | — |
| | 0.2 | — | 85 |
| H1 + 122 | 2.0 + 2.5 | 10 | — |
| | 0.2 + 2.5 | — | 20 |
| H1 + 148 | 2.0 + 2.5 | 50 | — |
| | 0.2 + 2.5 | — | 40 |
| H1 + 182 | 2.0 + 2.5 | 40 | — |
| H1 + 542 | 0.2 + 2.5 | — | 35 |
| | 2.0 + 2.5 | 30 | — |
| | 0.2 + 2.5 | — | 35 |
| H1 + 131 | 2.0 + 2.5 | 20 | — |
| | 0.2 + 2.5 | — | 40 |
| H1 + 191 | 2.0 + 2.5 | 20 | — |
| | 0.2 + 2.5 | — | 45 |
| H1 + 1 | 2.0 + 2.5 | 15 | — |
| | 0.2 + 2.5 | — | 45 |
| H1 + 782 | 2.0 + 2.5 | 20 | — |
| | 0.2 + 2.5 | — | 40 |
| H1 + 602 | 2.0 + 2.5 | 20 | — |
| | 0.2 + 2.5 | — | 50 |
| H1 + 1201 | 2.0 + 2.5 | 35 | — |
| | 0.2 + 2.5 | — | 50 |
| H1 + 611 | 2.0 + 2.5 | 35 | — |
| | 0.2 + 2.5 | — | 50 |
| H1 + 1202 | 2.0 + 2.5 | 50 | — |
| | 0.2 + 2.5 | — | 70 |
| H1 + 1142 | 2.0 + 2.5 | 25 | — |
| | 0.2 + 2.5 | — | 40 |
| H1 + 842 | 2.0 + 2.5 | 25 | — |
| | 0.2 + 2.5 | — | 30 |
| H1 + 902 | 2.0 + 2.5 | 50 | — |
| | 0.2 + 2.5 | — | 55 |
| H1 + 71 | 2.0 + 2.5 | 50 | — |
| | 0.2 + 2.5 | — | 65 |
| H1 + 632 | 2.0 + 2.5 | 30 | — |
| | 0.2 + 2.5 | — | 85 |
| H1 + 605 | 2.0 + 2.5 | 70 | — |
| | 0.2 + 2.5 | — | 40 |
| H1 + 722 | 2.0 + 2.5 | 20 | — |
| | 0.2 + 2.5 | — | 50 |
| H1 + 152 | 2.0 + 2.5 | 40 | — |
| | 0.2 + 2.5 | — | 85 |
| H1 + 212 | 2.0 + 2.5 | 40 | — |
| | 0.2 + 2.5 | — | 70 |
| H1 + 302 | 2.0 + 2.5 | 60 | — |
| | 0.2 + 2.5 | — | 30 |

TABLE 1-continued

Safener action of the compounds according to the invention

| Combination Herbicide/Safener | Dosage (kg of a.s./ha) | % damage (safener action) TA | % damage (safener action) HV |
|---|---|---|---|
| H1 + 362 | 2.0 + 2.5 | 20 | — |
|  | 0.2 + 2.5 | — | 20 |
| H1 + 1204 | 2.0 + 2.5 | 60 | — |
|  | 0.2 + 2.5 | — | 50 |
| H1 + 1205 | 2.0 + 2.5 | 60 | — |
|  | 0.2 + 2.5 | — | 50 |
| H1 + 1206 | 2.0 + 2.5 | 60 | — |
|  | 0.2 + 2.5 | — | 50 |
| H1 + 1207 | 2.0 + 2.5 | 55 | — |
|  | 0.2 + 2.5 | — | 45 |
| H1 + 1208 | 2.0 + 2.5 | 60 | — |
|  | 0.2 + 2.5 | — | 45 |
| H1 + 1209 | 2.0 + 2.5 | 70 | — |
|  | 0.2 + 2.5 | — | 45 |
| H1 + 422 | 2.0 + 2.5 | 70 | — |
|  | 0.2 + 2.5 | — | 50 |
| H1 + 1210 | 2.0 + 2.5 | 70 | — |
|  | 0.2 + 2.5 | — | 55 |
| H1 + 1211 | 2.0 + 2.5 | 60 | — |
|  | 0.2 + 2.5 | — | 50 |
| H1 + 1212 | 2.0 + 2.5 | 70 | — |
|  | 0.2 + 2.5 | — | 40 |
| H1 + 1213 | 2.0 + 2.5 | 40 | — |
|  | 0.2 + 2.5 | — | 30 |
| H1 + 1214 | 2.0 + 2.5 | 60 | — |
|  | 0.2 + 2.5 | — | 10 |
| H$_1$ + 121 | 2,0 + 2,5 | 25 | — |
|  | 0,2 + 2,5 | — | 40 |
| H$_1$ + 123 | " | 60 | — |
|  | " | — | 40 |
| H$_1$ + 124 | 2,0 + 1,25 | 20 | — |
|  | 0,2 + 1,25 | — | 30 |
| H$_1$ + 125 | 2,0 + 2,5 | 60 | — |
|  | 0,2 + 2,5 | — | 40 |
| H$_1$ + 127 | " | 40 | — |
|  | " | — | 30 |
| H$_1$ + 128 | 2,0 + 1,25 | 20 | — |
|  | 0,2 + 1,25 | — | 40 |
| H$_1$ + 132 | 2,0 + 2,5 | 30 | — |
|  | 0,2 + 2,5 | — | 30 |
| H$_1$ + 133 | 2,0 + 1,25 | 20 | — |
|  | 0,2 + 1,25 | — | 30 |
| H$_1$ + 135 | 2,0 + 2,5 | 30 | — |
|  | 0,2 + 2,5 | — | 30 |
| H$_1$ + 137 | 2,0 + 1,25 | 40 | — |
|  | 0,2 + 1,25 | — | 50 |
| H$_1$ + 138 | " | 10 | — |
|  | " | — | 20 |
| H$_1$ + 140 | " | 20 | — |
|  | " | — | 40 |
| H$_1$ + 143 | " | 15 | — |
|  | " | — | 60 |
| H$_1$ + 146 | 2,0 + 1,25 | 40 | — |
|  | 0,2 + 1,25 | — | 70 |
| H$_1$ + 147 | " | 20 | — |
|  | " | — | 20 |
| H$_1$ + 149 | " | 35 | — |
|  | " | — | 40 |
| H$_1$ + 150 | " | 30 | — |
|  | " | — | 80 |
| H$_1$ + 153 | " | 10 | — |
|  | " | — | 30 |
| H$_1$ + 157 | " | 50 | — |
|  | " | — | 75 |
| H$_1$ + 159 | " | 20 | — |
|  | " | — | 20 |
| H$_1$ + 160 | " | 50 | — |
|  | " | — | 60 |
| H$_1$ + 162 | " | 30 | — |
|  | " | — | 80 |
| H$_1$ + 164 | " | 10 | — |
|  | " | — | 70 |
| H$_1$ + 171 | " | 20 | — |
|  | " | — | 75 |
| H$_1$ + 242 | " | 20 | — |
|  | " | — | 30 |
| H$_1$ + 251 | " | 20 | — |
|  | " | — | 20 |
| H$_1$ + 301 | " | 20 | — |
|  | " | — | 30 |
| H$_1$ + 303 | " | 10 | — |
|  | " | — | 20 |
| H$_1$ + 311 | " | 30 | — |
|  | " | — | 30 |
| H$_1$ + 361 | 2,0 + 1,25 | 15 | — |
|  | 0,2 + 1,25 | — | 20 |
| H$_1$ + 391 | " | 25 | — |
|  | " | — | 50 |
| H$_1$ + 392 | " | 20 | — |
|  | " | — | 70 |
| H$_1$ + 482 | " | 20 | — |
|  | " | — | 40 |
| H$_1$ + 491 | " | 20 | — |
|  | " | — | 40 |
| H$_1$ + 511 | " | 30 | — |
|  | " | — | 85 |
| H$_1$ + 692 | " | 30 | — |
|  | " | — | 40 |
| H$_1$ + 1022 | " | 30 | — |
|  | " | — | 70 |
| H$_1$ + 1218 | 2,0 + 2,5 | 30 | — |
|  | 0,2 + 2,5 | — | 20 |
| H$_1$ + 1219 | " | 35 | — |
|  | " | — | 50 |
| H$_1$ + 1220 | " | 30 | — |
|  | " | — | 20 |
| H$_1$ + 1221 | " | 30 | — |
|  | " | — | 20 |
| H$_1$ + 1222 | " | 15 | — |
|  | " | — | 30 |
| H$_1$ + 1223 | " | 20 | — |
|  | " | — | 60 |
| H$_1$ + 1224 | " | 20 | — |
|  | " | — | 60 |
| H$_1$ + 1225 | " | 50 | — |
|  | " | — | 30 |
| H$_1$ + 1226 | 2,0 + 1,25 | 30 | — |
|  | 0,2 + 1,25 | — | 70 |
| H$_1$ + 1227 | " | 50 | — |
|  | " | — | 80 |
| H$_1$ + 1228 | " | 40 | — |
|  | " | — | 70 |
| H$_1$ + 1229 | " | 30 | — |
|  | " | — | 60 |
| H$_1$ + 1230 | " | 50 | — |
|  | " | — | 80 |
| H$_1$ + 1231 | " | 40 | — |
|  | " | — | 75 |
| H$_1$ + 1233 | " | 40 | — |
|  | " | — | 75 |
| H$_1$ + 1235 | " | 20 | — |
|  | " | — | 40 |
| H$_1$ + 1236 | " | 20 | — |
|  | " | — | 60 |

Abbreviations:
TA = Triticum aestivum (wheat)
HV = Hordeum vulgare (barley)
a.s. = active substance
H1 = fenoxaprop-ethyl

We claim:

1. An agent for protecting crop plants from the phytotoxic side effects of the herbicide ethyl 2-(4-(6-chlorobenzoxazol-2-yloxy)-phenoxy)-propionate, which agent comprises an amount effective for protecting crop plants from phytotoxic side effects of the herbicide, of the safener compound ethyl 1-(2,4-dichlorophenyl)-5-isopropyl-pyrazole-3-carboxylate in combination with the herbicide, in a weight ratio of safener to herbicide ethyl 2-(4-6-chlorobenzoxazol-2-yloxy)-phenoxy)-propionate of 1:1 to 1:10.

2. An agent for protecting crop plants from the phytotoxic side effects of the herbicide ethyl 2-(4-(6-chlorobenzoxazol-2-yloxy)-phenoxy)-propionate,
which agent comprises an amount effective for protecting crop plants from phytotoxic side effects of the herbicide, of the safener compound 1-(2,4-dichlorophenyl)-5-isopropyl-pyrazole-3-carboxylic acid in combination with the herbicide, in a weight ratio of safener to herbicide ethyl 2-(4-6-chlorobenzoxazol-2-yloxy)-phenoxy)-propionate of 1:1 to 1:10.

3. A method for protecting crop plants from phytotoxic side effects of the herbicide ethyl 2-(4-(6-chlorobenzoxazol-2-yloxy)-phenoxy)-propionate,
which comprises treating the plants, seeds of the plants or their cultivation areas with an effective amount of the safener compound ethyl 1-(2,4-dichlorophenyl)-5-isopropyl-pyrazole-3-carboxylate before, after, or at the same time, as treating with the herbicide, in a weight ratio of safener to herbicide ethyl 2-(4-6-chlorobenzoxazol-2-yloxy)-phenoxy)-propionate of 1:1 to 1:10.

4. A method for protecting crop plants from phytotoxic side effects of the herbicide ethyl 2-(4-(6-chlorobenzoxazol-2-yloxy)-phenoxy)-propionate,
which comprises treating the plants, seeds of the plants or their cultivation areas with an effective amount of the safener compound 1-(2,4-dichlorophenyl)-5-isopropyl-pyrazole-3-carboxylic acid before, after, or at the same time, as treating with the herbicide, in a weight ratio of safener to herbicide ethyl 2-(4-6-chlorobenzoxazol-2-yloxy)-phenoxy)-propionate of 1:1 to 1:10.

* * * * *